United States Patent
Kumar et al.

(10) Patent No.: US 10,799,604 B2
(45) Date of Patent: Oct. 13, 2020

(54) BIOPOLYMER-NANOPARTICLE COMPOSITE IMPLANT FOR TUMOR CELL TRACKING

(71) Applicants: Northeastern University, Boston, MA (US); The Brigham and Women's Hospital, Inc., Boston, MA (US); Dana-Farber Cancer Institute, Inc., Boston, MA (US)

(72) Inventors: Rajiv Kumar, Malden, MA (US); Srinivas Sridhar, Newton, MA (US); Wilfred Ngwa, Framingham, MA (US); Robert Cormack, Milton, MA (US); Gerassimos Makrigiorgos, Chestnut Hill, MA (US)

(73) Assignees: Northeastern University, Boston, MA (US); Dana-Farber Cancer Institute, Inc., Boston, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/328,711

(22) PCT Filed: Jul. 27, 2015

(86) PCT No.: PCT/US2015/042229
§ 371 (c)(1),
(2) Date: Jan. 24, 2017

(87) PCT Pub. No.: WO2016/015044
PCT Pub. Date: Jan. 28, 2016

(65) Prior Publication Data
US 2017/0209601 A1 Jul. 27, 2017

Related U.S. Application Data

(60) Provisional application No. 62/028,880, filed on Jul. 25, 2014.

(51) Int. Cl.
| | | |
|---|---|---|
| *A61K 49/00* | (2006.01) |
| *A61L 31/14* | (2006.01) |
| *A61K 49/04* | (2006.01) |
| *A61K 45/06* | (2006.01) |
| *A61L 31/04* | (2006.01) |
| *A61P 35/04* | (2006.01) |
| *A61K 9/00* | (2006.01) |
| *A61K 9/20* | (2006.01) |
| *A61B 90/00* | (2016.01) |
| *A61B 5/00* | (2006.01) |
| *A61K 31/337* | (2006.01) |
| *A61L 31/06* | (2006.01) |
| *A61L 31/16* | (2006.01) |
| *A61L 31/18* | (2006.01) |
| *A61N 5/10* | (2006.01) |

(52) U.S. Cl.
CPC ........ *A61K 49/0065* (2013.01); *A61B 5/4887* (2013.01); *A61B 90/39* (2016.02); *A61K 9/0024* (2013.01); *A61K 9/204* (2013.01); *A61K 31/337* (2013.01); *A61K 45/06* (2013.01); *A61K 49/0054* (2013.01); *A61K 49/04* (2013.01); *A61K 49/0423* (2013.01); *A61L 31/042* (2013.01); *A61L 31/048* (2013.01); *A61L 31/06* (2013.01); *A61L 31/14* (2013.01); *A61L 31/148* (2013.01); *A61L 31/16* (2013.01); *A61L 31/18* (2013.01); *A61N 5/1027* (2013.01); *A61P 35/04* (2018.01); *A61B 2090/3966* (2016.02); *A61L 2300/256* (2013.01); *A61L 2300/416* (2013.01); *A61L 2400/12* (2013.01); *A61N 2005/1023* (2013.01)

(58) Field of Classification Search
CPC ............ A61K 49/0065; A61K 49/0054; A61K 49/04; A61K 31/337; A61N 2005/1023; A61N 5/1027; A61L 2300/416; A61L 31/16; A61L 31/06; A61L 31/14; A61L 31/18; A61B 5/4887
See application file for complete search history.

(56) References Cited

U.S. PATENT DOCUMENTS

2003/0134810 A1   7/2003   Springate et al.
2009/0196831 A1   8/2009   Yang et al.
(Continued)

FOREIGN PATENT DOCUMENTS

WO   2007/027978 A2   3/2007
WO   2013/059528 A2   4/2013
(Continued)

OTHER PUBLICATIONS

W. J. Parak, et al., "Cell Motility and Metastatic Potential Studies Based on Quantum Dot Imaging of Phagokinetic Tracks", Adv. Mater., (2002), vol. 14, No. 12, pp. 882-885.
(Continued)

*Primary Examiner* — Robert S Cabral
(74) *Attorney, Agent, or Firm* — Verrill Dana, LLP

(57) ABSTRACT

A method of detecting migration of tumor cells is provided by implanting in a region of tumor cells one or more implants having a matrix material of a biocompatible and biodegradable polymer, and a plurality of nanoparticles dispersed within the matrix material and functionalized to bind tumor cells. Nanoparticles bound to the tumor cells that have migrated out of the region can be detected by various imaging modalities. The implant can be in the shape of a brachytherapy spacer or radiotherapy fiducial maker or can be a coating on a brachytherapy spacer or fiducial marker. A method of treating cancer is provided by implanting one or more brachytherapy spacers or fiducial markers including the matrix material and an anti-cancer therapeutic agent dispersed within the matrix material.

16 Claims, 15 Drawing Sheets

(56) References Cited

U.S. PATENT DOCUMENTS

| | | |
|---|---|---|
| 2009/0208580 A1 | 8/2009 | Shi et al. |
| 2012/0118751 A1 | 5/2012 | Cai et al. |
| 2012/0259153 A1 | 10/2012 | Wang et al. |
| 2013/0323165 A1 | 12/2013 | Campbell et al. |
| 2014/0072510 A1 | 3/2014 | Shea et al. |
| 2014/0134265 A1 | 5/2014 | Buggy et al. |

FOREIGN PATENT DOCUMENTS

| | | |
|---|---|---|
| WO | 2013/076305 A1 | 5/2013 |
| WO | 2013/112643 A1 | 8/2013 |
| WO | 2014021954 A2 | 2/2014 |

OTHER PUBLICATIONS

J.W.M. Bulte, et al., "Magnetodendrimers allow endosomal magnetic labeling and in vivo tracking of stem cells", Nature Biotechnology, Dec. 2001, vol. 19, pp. 1141-1147.

E. I. Galanzha, et al., "In vivo magnetic enrichment and multiplex photoacoustic detection of circulating tumour cells", Nature Nanotechnology, Dec. 2009, vol. 4, pp. 855-860.

M. Lewin, et al., "Tat peptide-derivatized magnetic nanoparticles allow in vivo tracking and recovery of progenitor cells", Nature Biotechnology, Apr. 2000, vol. 18, pp. 410-414.

J. Liu, et al., "A novel trans-lymphatic drug delivery system: Implantable gelatin sponge impregnated with PLGA-paclitaxel microspheres", Biomaterials, (2007), vol. 28, pp. 3236-3244.

Sunderland C. Targeted Nanoparticles for Detecting and Treating Cancer. Drug Development Research 67:70-93 (2006).

Wolinsky J et al. Local Drug Delivery Strategies for Cancer Treatment: Gels, Nanoparticles, Polymeric Films, Rods, and Wafers. J Control Release. Apr. 10, 2012; 159(1).

Ngwa W et al. Targeted radiotherapy with gold nanoparticles: current status and future perspectives. Nanomedicine (2014) 9(7), 1063-1082.

Kumar R. Third generation gold nanoplatform optimized for radiation therapy. Transl Cancer Res 2013;2(4):228-239.

Sinha N. et al. Brachytherapy Application With in Situ Dose Painting Administered by Gold Nanoparticle Eluters. Int J Radiation Oncol Biol Phys, vol. 91, No. 2, pp. 385-392, 2015.

Kumar R et al. Nanoparticle-Based Brachytherapy Spacers for Delivery of Localized Combined Chemoradiation Therapy. Int J Radiation Oncol Biol Phys, vol. 91, No. 2, pp. 393-400, 2015.

Huang X et al. Gold nanoparticles: interesting optical properties and recent applications in cancer diagnostics and therapy. Nanomedicine, 2007; 2(5):681-93.

Cai W et al. Applications of gold nanoparticles in cancer nanotechnology. Nanotechnology, Science and Applications, 2008:1 17-32.

Martin D et al. Nanoparticles for urothelium penetration and delivery of the histone deacetylase inhibitor belinostat for treatment of bladder cancer. Nanomedicine, Nov. 2013; 9(8):1124-34.

Wen S. Multifunctional dendrimer-entrapped gold nanoparticles for dual mode CT/MR imaging applications. Biomaterials, 2013, 34:1570-1580.

Maltez-Da-Costa M et al. Simple Monitoring of Cancer Cells Using Nanoparticles. Nano Lett., 2012, 12(8):4164-4171.

Mousa S et al. Nanotechnology-Based Detection and Targeted Therapy in Cancer: Nano-Bio Paradigms and Applications. Cancers, 2011, 3:2888-2903.

Li S. Novel theranostics based on hybrid nanoparticles for early cancer detection and treatment. Doctoral dissertation Aug. 2013. Retrieved from the Internet: hdl.handle.net/10722/195996.

Ma Y et al. Nanoparticles of Poly(Lactide-Co-Glycolide)-d-a-Tocopheryl Polyethylene Glycol 1000 Succinate Random Copolymer for Cancer Treatment. Nanoscale Research Letters, 2010, 5(7):1161-9.

Sukumar U et al. Emerging applications of nanoparticles for lung cancer diagnosis and therapy. International Nano Letters, 2013, 3:45.

Kumar S et al. Synthesis of PET-PLA/Drug Nanoparticles and Their Effect with Gold Nanoparticles for Controlled Drug Release in Cancer Chemotherapy. Research Letters in Nanotechnology, 2008, Article ID 389512, 4 pages.

Xu C et al. Tracking Mesenchymal Stem Cells with Iron Oxide Nanoparticle Loaded Poly(lactide-co-glycolide) Microparticles. Nano Lett., 2012, 12(8):4131-4139.

Zhanga F et al. Noninvasive monitoring of orthotopic glioblastoma therapy response using RGD-conjugated iron oxide nanoparticles. Biomaterials, Jul. 2012, 33(21):5414-5422.

Dianzani C et al. Drug Delivery Nanoparticles in Skin Cancers. BioMed Research International, 2014, Article ID 895986, 13 pages.

Kim D et al. A drug-loaded aptamer-gold nanoparticle bioconjugate for combined CT imaging and therapy of prostate cancer. ACS Nano, 2010, 4(7)3689-96.

Takae S et al. Ligand density effect on biorecognition by PEGylated gold nanoparticles: regulated interaction of RCA120 lectin with lactose installed to the distal end of tethered PEG strands on gold surface. Biomacromolecules. 2005; 6(2):818-24.

Azizian G et al. Synthesis route and three different core-shell impacts on magnetic characterization of gadolinium oxide-based nanoparticles as new contrast agents for molecular magnetic resonance imaging. Nanoscale Research Letters, 2012, 7:549.

Kirui D et al. PAA-Derived Gold Nanorods for Cellular Targeting and Photothermal Therapy. Macromolecular Bioscience, 2011, 11(6):779-788.

De Jong W et al. Drug delivery and nanoparticles: Applications and hazards. Int J Nanomedicine, 2008, 3(2):133-149.

Shenoy D et al. Surface functionalization of gold nanoparticles using hetero-bifunctional poly(ethylene glycol) spacer for intracellular tracking and delivery. Int J Nanomedicine, 2006, 1(1):51-57.

Kulkarni A. Modification of gold markers with Doxorubicin as Radiosensitizer encapsulated in sustained release PLGA nanoparticles to enhance Image Guided Radiotherapy (IGRT). Pharmaceutical Science Master's Theses, Northeastern University, 2011. Retrieved from the Internet: hdl.handle.net/2047/d20001246.

Nagesha D et al. Radiosensitizer-eluting nanocoatings on gold fiducials for biological in-situ image-guided radio therapy (BIS-IGRT). Physics in Medicine and Biology, 2010, 55(20):6039-52.

Berbeco R et al. DNA Damage Enhancement from Gold Nanoparticles for Clinical MV Photon Beams. Radiation Research, 2012, 178(6):604-608.

Kumar R et al. Localized tumor delivery of radiosensitizers and chemotherapeutics using 'INCeRT' implants. Mol Cancer Ther. 2013, 12(11 Supplement):A82. Abstract.

Ngwa W et al. Toward Customizable Radiation Therapy Enhancement (CuRE) With Gold Nanoparticles Released, In Situ, From Gold-Loaded Brachytherapy Spacers. International Journal of Radiation Oncology. Oct. 1, 2013,87(2):S151.

BIOPOLYMER-NANOPARTICLE COMPOSITE IMPLANT FOR TUMOR CELL TRACKING

CROSS REFERENCE TO RELATED APPLICATIONS

This application claims priority under 35 § 119(e) of U.S. Provisional Application No. 62/028,880, filed on Jul. 25, 2014, entitled "Biomaterial for Response Assessment and Nodal Detection (BRAND)", the disclosure of which is hereby incorporated by reference.

STATEMENT REGARDING FEDERALLY SPONSORED RESEARCH OR DEVELOPMENT

This invention was made with government support under Grant Number CA172478 awarded by the National Institutes of Health. The government has certain rights in the invention.

BACKGROUND

Metastasis is the spread of cancer from the primary site (the source tumor) to one or more other parts of the body. Metastasis accounts for over 90% of all cancer-associated suffering and death, and it presents the most significant challenges in the management of cancer.

Circulating tumor cells (CTCs) can serve as biological markers (biomarkers) for non-invasive early detection of metastasis, tumor aggressiveness, tumor response to treatment, or prognosis, and can enhance understanding of the biology of metastasis. The ultimate goal, to efficiently detect and isolate the rare population of tumor cells in a viable state and with high purity from the vast number of surrounding blood cells, still presents a formidable technological challenge. Also, metastasis in sentinel lymph nodes is considered an important prognostic factor in cancer, such as pelvic lymph nodes for prostate cancer (PCa), and a reflection of the aggressiveness of a tumor. Despite the importance of the nodal status, methods to assess lymph nodes are suboptimal. Current lymph node staging via lymphadenectomy is accompanied by significant morbidities. Computed tomography (CT) and magnetic resonance imaging (MRI) are useful in evaluating anatomical abnormalities; however, neither technology can differentiate between adenopathy related to inflammation and that cause by deposition of CTCs.

SUMMARY OF THE INVENTION

The invention relates to labeling, tracking, and treating metastatic tumor cells in a patient.

In one aspect, a method of detecting migration of tumor cells includes steps of implanting one or more implants in a region of tumor cells. The implant includes a matrix material comprising a biocompatible and biodegradable polymer and a plurality of nanoparticles dispersed within the matrix and functionalized to bind the tumor cells. The functionalized nanoparticles are conjugated to a tumor-targeting moiety and in some cases also to a detection moiety. The method also includes the step of detecting the nanoparticles bound to tumor cells that have migrated out of the region.

In another aspect, a method of treating cancer includes implanting one or more brachytherapy spacers or radiotherapy fiducial markers in a region of tumor cells, the spacer or marker including a matrix material comprising a biocompatible and biodegradable polymer and an anti-cancer therapeutic agent dispersed within the matrix material.

Other aspects of the method and system include the following:

1. A method of detecting migration of tumor cells, comprising:
   (a) implanting one or more implants in a region of tumor cells in a patient in need thereof, the implant comprising:
      a matrix material comprising a biocompatible and biodegradable polymer, and
      a plurality of nanoparticles functionalized to bind said tumor cells, the nanoparticles dispersed within the matrix material, the functionalized nanoparticles conjugated to a tumor-targeting moiety; and
   (b) detecting the nanoparticles bound to said tumor cells that have migrated out of said region.

2. The method of item 1, wherein the functionalized nanoparticles are further conjugated to a detection moiety.

3. The method of any of items 1-2, wherein the detection moiety is selected from the group consisting of a fluorophore, radiolabel, and magnetic resonance contrast agent.

4. The method of any of items 1-3 wherein the tumor-targeting moiety and the detection moiety and embodied in a single molecule.

5. The method of any of items 1-4, wherein the tumor-targeting moiety is selected from the group consisting of a tumor-targeting ligand, peptide, protein, aptamer, oligonucleotide, antibody, cell adhesion molecule, small molecule, and combinations thereof.

6. The method of any of items 1-5, wherein the tumor-targeting ligand is selected from the group consisting of folic acid, a ligand for epidermal growth factor receptor, transferrin, an RGD peptide, PSMA aptamer, and combinations thereof.

7. The method of any of items 1-6, wherein the functionalized nanoparticles comprise a surface coating of heterobifunctional-polyethylene glycol derivative comprising an amine, carboxyl, thiol, hydroxyl, or methoxy functional group.

8. The method of any of items 1-7, wherein the detecting step comprises use of photoacoustic imaging, surface enhanced Raman spectroscopy, X-ray computed tomography, magnetic resonance imaging, positron emission tomography, single-photon emission computed tomography, fluorescence imaging, optical coherence tomography, or ultrasound imaging.

9. The method of any of items 1-8, wherein the functionalized nanoparticles are conjugated with a fluorescent dye, and the detecting step comprises using fluorescence imaging.

10. The method of any of items 1-9, wherein the functionalized nanoparticles comprise gold and are conjugated with rhodamine B or 4-mercaptobenzoic acid, and the detecting step comprises using surface enhanced Raman spectroscopy.

11. The method of any of items 1-10, wherein the functionalized nanoparticles comprise gadolinium or iron-oxide and the detecting step comprises using magnetic resonance imaging.

12. The method of any of items 1-10, wherein the functionalized nanoparticles comprise gold and the detecting step comprises using X-ray computed tomography.

13. The method of any of items 1-10, wherein the functionalized nanoparticles are conjugated with poly(lactic acid) and the detecting step comprises using ultrasound imaging.

14. The method of any of items 1-13, wherein the implant is a brachytherapy spacer or a radiotherapy fiducial marker.

15. The method of any of items 1-14, wherein the brachytherapy spacer comprises a core, the matrix material and nanoparticles disposed surrounding the core.

16. The method of any of items 1-15, wherein the matrix material and nanoparticles comprise a coating having a thickness ranging from 0.1 mm to 1.0 mm.

17. The method of any of items 1-16, wherein the core comprises an inert material.

18. The method of any of items 1-17, wherein the inert material comprises an acrylic resin, a polyacrylate, or a polyethylene.

19. The method of any of items 1-18, wherein the implant is elongated and has a length ranging from 2 mm to 8 mm.

20. The method of any of items 1-19, wherein the length is about 5 mm.

21. The method of any of items 1-20, wherein the implant is cylindrical and has a diameter ranging from about 0.5 to about 1.5 mm.

22. The method of any of items 1-21, wherein the diameter is about 0.8 mm.

23. The method of any of items 1-22, wherein the implant is elongated and has an aspect ratio ranging from 0.05 to 0.75.

24. The method of any of items 1-18, wherein the implant has a shape of a rod, a cylinder, a bar, a cube, a rectangle, a sphere, a shell, or an ellipse.

25. The method of any of items 1-18, wherein the implant has a shape corresponding to a shape of a brachytherapy spacer or a radiotherapy fiducial marker.

26. The method of any of items 1-3, wherein the implant comprises a gel.

27. The method of any of item 26, wherein the gel is selected from the group consisting of a polyethylene glycol, polyacrylic acid, polyacrylamide, poly(N-isopropylacrylamide), hyaluronic acid, and combinations thereof.

28. The method of any of items 1-27, wherein the tumor cells are present in a primary tumor.

29. The method of any of items 1-28, wherein the tumor cells are from prostate cancer, lung cancer, pancreatic cancer, liver cancer, breast cancer, ovarian cancer, gastric cancer, colon cancer, brain cancer, or head and neck cancer.

30. The method of any of items 1-29, wherein the nanoparticles are detected in tumor cells in a blood vessel, in a lymphatic vessel, in a lymphatic node, in a lymphatic organ, or at a metastatic site in a region of the patient to which the tumor cells have migrated.

31. The method of any of items 1-30, wherein the matrix material biodegrades after implantation at a rate ranging from 1 to 60 days.

32. The method of any of items 1-30, wherein the matrix material biodegrades after implantation at a rate ranging from 1 to 120 days.

33. The method of any of items 1-32, wherein the matrix material comprises a polymer or co-polymer of lactide, glycolide, or a combination thereof.

34. The method of any of items 1-32, wherein the matrix comprises a polyester of hydroxycarboxylic acids.

35. The method of any of items 1-33, wherein the matrix material is selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, and polyamine, chitosan and combinations thereof.

36. The method of any of items 1-35, wherein the functionalized nanoparticles are selected from the group consisting of gold, gadolinium, and iron-oxide.

37. The method of any of items 1-36, wherein the functionalized nanoparticles have a diameter ranging from about 1 nanometer to about 999 nanometers.

38. The method of any of items 1-37, wherein the functionalized nanoparticles are present in the matrix material in a concentration ranging from 0.001 to 10 mg per implant.

39. The method of any of items 1-38, wherein the implant further comprises a therapeutic agent.

40. The method of any of items 1-39, wherein the therapeutic agent is an anti-cancer agent.

41. The method of any of items 1-40, wherein the therapeutic agent is selected from the group consisting of docetaxel, paclitaxel, doxorubicin, cisplatin, gemcitabine, a hydrophobic drug, an anti-androgen compound, a small molecule signaling pathway inhibitor, and combinations thereof.

42. The method of any of items 1-41, wherein the anti-androgen compound is selected from the group consisting of enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.

43. The method of any of items 1-41, wherein the small molecule signaling pathway inhibitor is selected from the group consisting of a PI3K inhibitor, a PARP inhibitor, a PI3K/AKT/mTOR pathway inhibitor, and combinations thereof.

44. The method of any of items 1-43, wherein the implant has a diameter ranging from 0.5 mm to 1.5 mm, and the therapeutic agent is present in the matrix material at a concentration ranging from 250 to 500 µg/mm length of the implant.

45. The method of any of items 1-44, wherein the therapeutic agent is used with synchronous radiation therapy.

46. The method of any of items 1-45, wherein the radiation therapy comprises external beam radiation therapy, brachytherapy, stereotactic ablative radiotherapy, or intensity modulated radiation therapy.

47. The method of any of items 1-46, wherein the implant further includes a binder.

48. The method of any of items 1-47, wherein the binder is polyacrylamide.

49. The method of any of items 1-48, wherein the implant further includes an inert material selected to tune release properties.

50. The method of any of items 1-49, wherein the inert material comprises silica or a bone material.

51. The method of any of items 1-50, wherein the bone material is selected from the group consisting of hydroxyapatite, a calcium salt, a phosphate salt, and combinations thereof.

52. The method of any of items 1-51, wherein in step (a), the implant is injected into the region of tumor cells.

53. The method of any of items 1-52, wherein the implant is injected through a brachytherapy needle into the region of tumor cells.

54. The method of any of items 1-53, further comprising injecting radioactive brachytherapy seeds into the region of tumor cells.

55. The method of any of items 1-54, wherein step (b) occurs a period of time after step (a).

56. The method of any of items 1-55, wherein the period of time in step (b) is about 1 day.

57. The method of any of items 1-55, wherein the period of time in step (b) is about 1 week.

58. The method of any of items 1-55, wherein the period of time in step (b) is about 1 month.

59. The method of any of items 1-55, wherein the period of time in step (b) is about 3 months.

60. The method of any of items 1-59, further comprising detecting a metastasis and treating the metastasis.

61. An implant for detecting migration of tumor cells, comprising:
an elongated body having a length ranging from 2 mm to 8 mm and a diameter ranging from 0.5 mm to 1.5 mm, comprising:
a matrix material comprising a biocompatible and biodegradable polymer, and
a plurality of nanoparticles functionalized to bind said tumor cells, the nanoparticles dispersed within the matrix material, the nanoparticles conjugated to a tumor-targeting moiety.

62. The implant of item 61, wherein the implant is a brachytherapy spacer or a radiotherapy fiducial marker.

63. The implant of any of items 61-62, wherein the brachytherapy spacer comprises a core, the matrix material and nanoparticles disposed surrounding the core.

64. The implant of any of items 61-63, wherein the core comprises an inert material.

65. The implant of any of items 61-64, wherein the inert material comprises an acrylic resin, polyacrylate, or polyethylene.

66. The implant of any of items 61-65, wherein the length is about 5 mm.

67. The implant of any of items 61-66, wherein the diameter is about 0.8 mm.

68. The implant of any of items 61-67, wherein the implant is elongated and has an aspect ratio ranging from 0.05 to 0.75.

69. The implant of any of items 61-68, wherein in the implanting step, the implant has a shape of a rod, a cylinder, a bar, or a rectangle.

70. The implant of any of items 61-69, wherein the implant has a shape corresponding to a shape of a brachytherapy spacer or a radiotherapy fiducial marker.

71. The implant of any of items 61-70, wherein the matrix material biodegrades after implantation at a rate ranging from 1 to 60 days.

72. The implant of any of items 61-70, wherein the matrix material biodegrades after implantation at a rate ranging from 1 to 120 days.

73. The implant of any of items 61-72, wherein the matrix material comprises a polymer or co-polymer of lactide, glycolide, or a combination thereof.

74. The implant of any of items 61-72, wherein the matrix comprises a polyester of hydroxycarboxylic acids.

75. The implant of any of items 61-73, wherein the matrix material is selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, and combinations thereof.

76. The implant of any of items 61-75, wherein the functionalized nanoparticles are selected from the group consisting of gold, gadolinium, iron-oxide, and combinations thereof.

77. The implant of any of items 61-76, wherein the functionalized nanoparticles comprise a surface coating of hetero-bifunctional-polyethylene glycol derivative comprising an amine, carboxyl, thiol, hydroxyl, or methoxy functional group.

78. The implant of any of items 61-77, wherein the tumor-targeting moiety is selected from the group consisting of a tumor-targeting ligand, peptide, protein, aptamer, oligonucleotide, antibody, cell adhesion molecule, small molecule, and combinations thereof.

79. The implant of any of items 61-78, wherein the nanoparticles are conjugated to a detection moiety.

80. The implant of any of items 61-79, wherein the detection moiety is selected from the group consisting of a fluorophore, radiolabel, magnetic resonance contrast agent, and combinations thereof.

81. The implant of any of items 61-80, wherein the tumor-targeting moiety and the detection moiety and embodied in a single molecule.

82. The implant of any of items 61-81, wherein the tumor-targeting ligand is selected from the group consisting of folic acid, a ligand for an epidermal growth factor receptor, transferrin, an RGD peptide, PSMA aptamer, and combinations thereof.

83. The implant of any of items 61-82, wherein the functionalized nanoparticles have a diameter ranging from about 1 nanometer to about 999 nanometers.

84. The implant of any of items 61-83, wherein the functionalized nanoparticles are present in the matrix material in a concentration ranging from 0.001 to 10 mg per implant.

85. The implant of any of items 61-84, wherein the implant further comprises a therapeutic agent.

86. The implant of any of items 61-85, wherein the therapeutic agent is an anti-cancer agent.

87. The implant of any of items 61-86, wherein the therapeutic agent is selected from the group consisting of docetaxel, paclitaxel, doxorubicin, cisplatin, gemcitabine, a hydrophobic drug, an anti-androgen compound, a small molecule signaling pathway inhibitor, and combinations thereof.

88. The method of any of items 61-87, wherein the anti-androgen compound is selected from the group consisting of enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.

89. The method of any of items 61-87, wherein the small molecule signaling pathway inhibitor is selected from the group consisting of a PI3K inhibitor, a PARP inhibitor, a PI3K/AKT/mTOR pathway inhibitor, and combinations thereof.

90. The implant of any of items 61-89, wherein the implant has a diameter ranging from 0.5 mm to 1.5 mm, and the therapeutic agent is present in the matrix material at a concentration ranging from 250 to 500 µg/mm length of implant.

91. The implant of any of items 61-90, wherein the implant further includes a binder.

92. The implant of any of items 61-91, wherein the binder is polyacrylamide.

93. The implant of any of items 61-92, wherein the implant further includes inert materials selected to tune release properties.

94. The implant of any of items 61-93, wherein the inert materials comprises silica or a bone material.

95. The implant of any of items 61-94, wherein the bone material is selected from the group consisting of hydroxyapatite, a calcium salt, a phosphate salt, and combinations thereof.

96. A kit for detecting migration of tumor cells, comprising:
the implant of any of items 61-95 and a needle for injecting the implant into a region of tumor cells.

97. The kit of item 96, wherein the needle is a brachytherapy needle.

98. The kit of any of items 96 and 97, further comprising radioactive brachytherapy seeds.

99. A method of making an implant for detecting migration of tumor cells, comprising:
(a) providing a mixture comprising:
   a matrix material comprising a biocompatible and biodegradable polymer, and
   nanoparticles functionalized to bind said tumor cells, the nanoparticles dispersed within the matrix material, the nanoparticles conjugated to a tumor-targeting moiety; and
(b) forming an elongated body from the mixture having a length of 2 mm to 8 mm and a diameter ranging from 0.5 mm to 1.5 mm.

100. The method of item 99, wherein forming the elongated body further comprises:
   forming the mixture into a tube;
   solidifying the mixture; and
   cutting the tube into shorter lengths of 2 mm to 8 mm.

101. The method of any of items 99-100, wherein forming the mixture into a tube comprises infusing the mixture into a length of tubing.

102. The method of any of items 99-101, wherein forming the mixture into a tube comprises extruding the mixture as the tube.

103. The method of any of items 99-102, wherein forming the elongated body further comprises coating a core with the mixture of the functionalized nanoparticles dispersed within the matrix material.

104. The method of any of items 99 and 103, wherein forming the elongated body further comprises molding the mixture in a mold.

105. The method of any of items 99-104, wherein the elongated body is loaded into a syringe.

106. The method of any of items 99-105, wherein the syringe is a brachytherapy syringe or a radiotherapy fiducial marker syringe.

107. The method of any of items 99-106, further comprising loading the syringe with radioactive brachytherapy seeds.

108. The method of any of items 99-107, wherein the matrix material comprises a polymer or co-polymer of lactide, glycolide, or a combination thereof.

109. The method of any of items 99-108, wherein the matrix comprises a polyester of hydroxycarboxylic acids.

110. The method of any of items 99-109, wherein the matrix material is selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, and combinations thereof.

111. The method of any of items 99-110, wherein the functionalized nanoparticles are selected from the group consisting of gold, gadolinium, iron-oxide, and combinations thereof.

112. The method of any of items 99-111, wherein the functionalized nanoparticles are functionalized with a surface coating of hetero-bifunctional-polyethylene glycol with an amine, carboxyl, thiol, hydroxyl, or methoxy functional group.

113. The method of any of items 99-112, wherein the functionalized nanoparticles are conjugated to a detection moiety.

114. The method of any of items 99-113, wherein the detection moiety is selected from the group consisting of a fluorophore, radiolabel, magnetic resonance contrast agent, and combinations thereof.

115. The method of any of items 99-114, wherein the tumor-targeting moiety and the detection moiety are embodied in a single molecule.

116. The method of any of items 99-115, wherein the targeting moiety is selected from the group consisting of a tumor-targeting ligand, peptide, protein, aptamer, oligonucleotide, antibody, cell adhesion molecule, small molecule, and combinations thereof.

117. The method of any of items 99-116, wherein the tumor-targeting ligand is selected from the group consisting of folic acid, a single-chain variable fragment antibody, epidermal growth factor receptor, human protein transferrin, RGD peptide, small molecule, hyaluronic acid, riboflavin, PSMA aptamer, galactose derivatives, and combinations thereof.

118. The method of any of items 99-117, wherein the functionalized nanoparticles have a diameter ranging from about 1 nanometer to about 999 nanometers.

119. The method of any of items 99-118, wherein the functionalized nanoparticles are present in the matrix material in a concentration ranging from 0.001 to 10 mg per implant.

120. The method of any of items 99-119, wherein the mixture further includes an anti-cancer therapeutic agent dispersed within the matrix material.

121. The method of any of items 99-120, wherein the anti-cancer therapeutic agent is selected from the group consisting of docetaxel, paclitaxel, doxorubicin, cisplatin, gemcitabine, a hydrophobic drug, anti-androgen compound, small molecule signaling pathway inhibitor, and combinations thereof.

122. The method of any of items 99-121, wherein the anti-androgen compound is selected from the group consisting of enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.

123. The method of any of items 99-122, wherein the small molecule signaling pathway inhibitor is selected from the group consisting of a PI3K inhibitor, a PARP inhibitor, a PI3K/AKT/mTOR pathway inhibitor, and combinations thereof.

124. The method of any of items 99-123, wherein the implant has a diameter ranging from 0.5 mm to 1.5 mm, and the therapeutic agent is present in the matrix material at a concentration ranging from 250 to 500 µg/mm length of implant.

125. The method of any of items 99-124, wherein the implant further includes a binder.

126. The method of any of items 99-125, wherein the binder is polyacrylamide.

127. The method of any of items 99-126, wherein the implant further includes an inert material selected to tune release properties.

128. The method of any of items 99-127, wherein the inert material comprises silica or a bone material.

129. The method of any of items 99-128, wherein the bone material is selected from the group consisting of hydroxyapatite, a calcium salt, a phosphate salt, and combinations thereof.

130. A method of treating cancer, comprising:
  implanting one or more brachytherapy spacers or radiotherapy fiducial markers in a region of tumor cells in a patient in need thereof, the brachytherapy spacer or radiotherapy fiducial marker comprising:
    a matrix material comprising a biocompatible and biodegradable polymer, and
    an anti-cancer therapeutic agent dispersed within the matrix material.
131. The method of item 130, wherein the brachytherapy spacer or radiotherapy fiducial marker comprises a core, the matrix material and anti-cancer therapeutic agent disposed surrounding the core.
132. The method of any of items 130-131, wherein the core comprises an inert material.
133. The method of any of items 130-132, wherein the inert material comprises an acrylic resin, polyacrylate, or polyethylene.
134. The method of any of items 130-133, wherein the core comprises a radiopaque material.
135. The method of any of items 130-134, wherein the implant is elongated and has a length ranging from 2 mm to 8 mm.
136. The method of any of items 130-135, wherein the length is about 5 mm.
137. The method of any of items 130-137, wherein the implant is cylindrical and has a diameter ranging from about 0.5 to about 1.5 mm.
138. The method of any of items 130-137, wherein the diameter is about 0.8 mm.
139. The method of any of items 130-138, wherein the implant is elongated and has an aspect ratio ranging from 0.05 to 0.75.
140. The method of any of items 130-134, wherein in the implanting step, the implant has a shape of a rod, a cylinder, a bar, a cube, a rectangle, a sphere, a shell, or an ellipse.
141. The method of any of items 130-140, wherein the tumor cells are present in a primary tumor.
142. The method of any of items 130-141, wherein the tumor cells are from prostate cancer, lung cancer, pancreatic cancer, liver cancer, breast cancer, ovarian cancer, gastric cancer, colon cancer, brain cancer, or head and neck cancer.
143. The method of any of items 130-142, wherein the brachytherapy spacer of the radiotherapy fiducial marker further comprises a plurality of nanoparticles functionalized to bind said tumor cells, the nanoparticles dispersed within the matrix material, the nanoparticles conjugated to a tumor-targeting moiety.
144. The method of any of items 130-143, wherein the nanoparticles are detected in tumor cells in a blood vessel, in a lymphatic vessel, in a lymph node, in a lymphatic organ, or at a metastatic site in a region of the patient to which the tumor cells have migrated.
145. The method of any of items 130-144, wherein the matrix material biodegrades after implantation at a rate ranging from 1 to 60 days.
146. The method of any of items 130-144, wherein the matrix material biodegrades after implantation at a rate ranging from 1 to 120 days.
147. The method of any of items 130-146, wherein the matrix material comprises a polymer or co-polymer of lactide, glycolide, or a combination thereof.
148. The method of any of items 130-147, wherein the matrix comprises a polyester of hydroxycarboxylic acids.
149. The method of any of items 130-147, wherein the matrix material is selected from the group consisting of polylactide, polyglycolide, polylactide co-glycolide, polyester amides of glycolic or lactic acids, poly(N-isopropylacrylamide), polygalactin, polydioxanone, polyester, polyacrylate, polymethacrylate, polyvinyl alcohol, polyether, polyamine, chitosan, and combinations thereof.
150. The method of any of items 130-149, wherein the therapeutic agent is selected from the group consisting of docetaxel, paclitaxel, doxorubicin, cisplatin, gemcitabine, a hydrophobic drug, an anti-androgen compound, a small molecule signaling pathway inhibitor, and combinations thereof.
151. The method of any of items 130-150, wherein the therapeutic agent is an anti-androgen compound.
152. The method of any of items 130-151, wherein the anti-androgen compound is selected from the group consisting of enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.
153. The method of any of items 130-152, wherein the therapeutic agent is a small molecule signaling pathway inhibitor.
154. The method of any of items 130-153, wherein the small molecule signaling pathway inhibitor is selected from the group consisting of a PI3K inhibitor, a PARP inhibitor, a PI3K/AKT/mTOR pathway inhibitor, and combinations thereof.
155. The method of any of items 130-154, wherein the implant has a diameter ranging from 0.5 mm to 1.5 mm, and the therapeutic agent is present in the matrix material at a concentration ranging from 250 to 500 µg/mm length of implant.
156. The method of any of items 130-155, wherein the implant is injected through a brachytherapy needle into the region of tumor cells.
157. The method of any of items 130-156, further comprising injecting radioactive brachytherapy seeds into the region of tumor cells.
158. The method of any of items 130-157, wherein the therapeutic agent is used with synchronous radiation therapy.
159. The method of any of items 130-158, wherein the radiation therapy comprises external beam radiation therapy, brachytherapy, stereotactic ablative radiotherapy, or intensity modulated radiation therapy.
160. A method of making an implant for treating cancer, comprising:
  (a) providing a mixture comprising:
    a matrix material comprising a biocompatible and biodegradable polymer, and
    an anti-cancer therapeutic agent dispersed within the matrix material; and
  (b) forming an elongated body from the mixture having a length of 2 mm to 8 mm and a diameter ranging from 0.5 mm to 1.5 mm.
161. The method of item 160, wherein forming the elongated body further comprises:
  forming the mixture into a tube;
  solidifying the mixture; and
  cutting the tube into shorter lengths of 2 mm to 8 mm.
162. The method of any of items 160-161, wherein forming the mixture into a tube comprises infusing the mixture into a length of tubing.
163. The method of any of items 160-163, wherein forming the mixture into a tube comprises extruding the mixture as the tube.

164. The method of any of items 160-163, wherein forming the elongated body further comprises coating a core with the mixture.
165. The method of any of items 160-161, wherein forming the elongated body further comprises molding the mixture in a mold.
166. The method of any of items 160-165, wherein the elongated body is loaded into a syringe.
167. The method of any of items 160-166, wherein the syringe is a brachytherapy syringe or a radiotherapy fiducial marker syringe.
168. The method of any of items 160-167, further comprising loading the syringe with radioactive brachytherapy seeds.
169. The method of any of items 160-168, wherein the anti-cancer therapeutic agent is selected from the group consisting of docetaxel, paclitaxel, doxorubicin, cisplatin, gemcitabine, a hydrophobic drug, an anti-antigen compound, a small molecule signaling pathway inhibitor, and combinations thereof.
170. The method of any of items 160-169, wherein the anti-cancer therapeutic agent comprises an anti-androgen compound.
171. The method of any of items 160-170, wherein the anti-androgen compound is selected from the group consisting of enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.
172. The method of any of items 160-171, wherein the anti-cancer therapeutic agent comprises a small molecule signaling pathway inhibitor.
173. The method of any of items 160-172, wherein the small molecule signaling pathway inhibitor is selected from the group consisting of a PI3K inhibitor, a PARP inhibitor, a PI3K/AKT/mTOR pathway inhibitor, and combinations thereof.
174. The method of any of items 160-173, wherein the implant has a diameter ranging from 0.5 mm to 1.5 mm, and the therapeutic agent is present in the matrix material at a concentration ranging from 250 to 500 µg/mm length of implant.
175. The method of any of items 160-174, wherein the matrix material comprises a polymer or co-polymer of lactide, glycolide, or a combination thereof.
176. The method of any of items 160-175, wherein the matrix comprises a polyester of hydroxycarboxylic acids.
177. The method of any of items 160-175, wherein the matrix material is selected from the group consisting of polylactide, polyglycolide, polylactide co-glycolide, polyester amides of glycolic or lactic acids, poly(N-isopropylacrylamide), polygalactin, polydioxanone, polyesters, polyacrylate, polymethacrylate, polyvinyl alcohol, polyether, polyamine, chitosan, and combinations thereof.
178. The method of any of items 160-177, wherein the mixture further comprises a plurality of nanoparticles functionalized to bind tumor cells, the nanoparticles dispersed within the matrix material, the functionalized nanoparticles conjugated to a tumor-targeting moiety and a detection moiety.
179. The method of any of items 160-178, wherein the functionalized nanoparticles are selected from the group consisting of gold, gadolinium, iron-oxide, and combinations thereof.
180. The method of any of items 160-179, wherein the functionalized nanoparticles are functionalized with a surface coating of hetero-bifunctional-polyethylene glycol with an amine, carboxyl, thiol, hydroxy, or methoxy functional group.
181. The method of any of items 160-180, wherein the tumor-targeting moiety is selected from the group consisting of a tumor-targeting ligand, peptide, protein, aptamer, oligonucleotide, antibody, cell adhesion molecule, small molecule, and combinations thereof.
182. The method of any of items 160-181, wherein the detection moiety is selected from the group consisting of a fluorophore, radiolabel, magnetic resonance contrast agent, and combinations thereof.
183. The method of any of items 160-182, wherein the tumor-targeting ligand is selected from the group consisting of folic acid, a single-chain variable fragment antibody, epidermal growth factor receptor, human protein transferrin, peptide RGD, small molecule, hyaluronic acid, riboflavin, PSMA aptamer, galactose derivative, and combinations thereof.
184. The method of any of items 160-183, wherein the tumor-targeting moiety and the detection moiety and embodied in a single molecule.
185. The method of any of items 160-184, wherein the functionalized nanoparticles have a diameter ranging from about 1 nanometer to about 999 nanometers.
186. The method of any of items 160-185, wherein the functionalized nanoparticles are present in the matrix material in a concentration ranging from 0.001 to 10 mg per implant.
187. The method of any of items 160-186, wherein the implant further includes a binder.
188. The method of any of items 160-187, wherein the binder is polyacrylamide.
189. The method of any of items 160-188, wherein the implant further includes an inert material selected to tune release properties.
190. The method of any of items 160-189, wherein the inert materials comprises silica or a bone material.
191. The method of any of items 160-190, wherein the bone material is selected from the group consisting of hydroxyapatite, a calcium salt, a phosphate salt, and combinations thereof.

DESCRIPTION OF THE DRAWINGS

The invention will be more fully understood from the following detailed description taken in conjunction with the accompanying drawings in which.

DETAILED DESCRIPTION OF THE INVENTION

Figure 1C:
FIGS. 1A, 1B, and 1C are schematic illustrations of an embodiment of an implant with a polymer matrix material degrading over time to release functionalized nanoparticles.
Figure 1B:
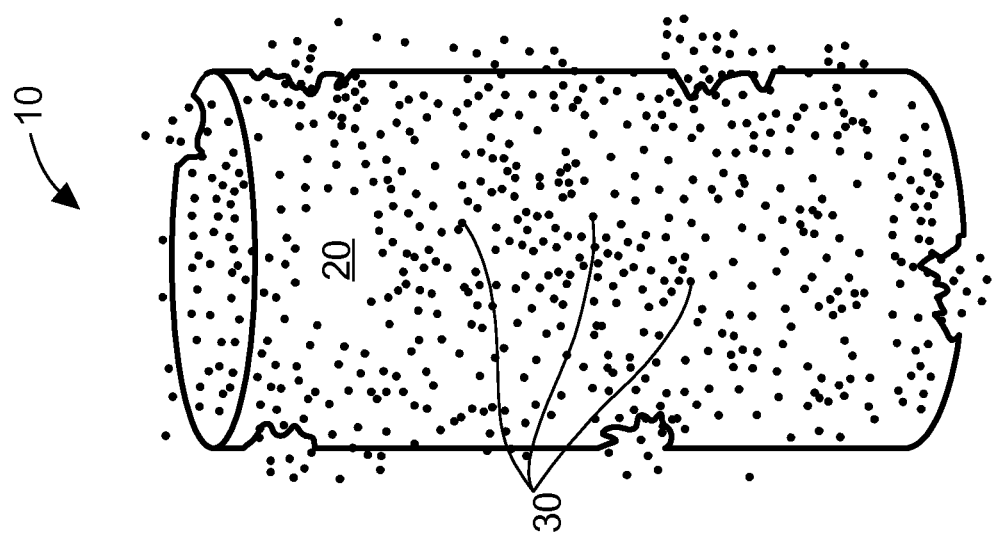
Figure 1A:
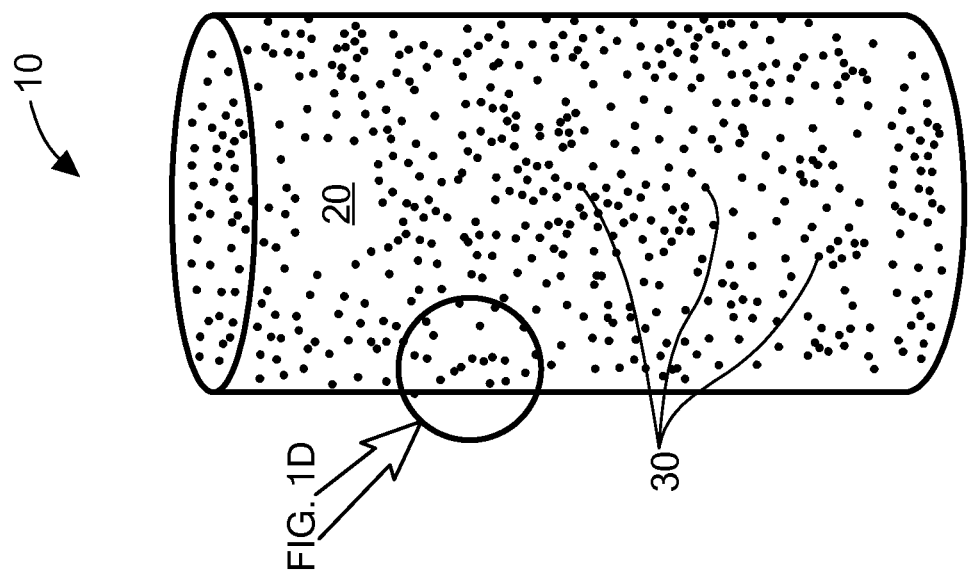
Figure 1D:
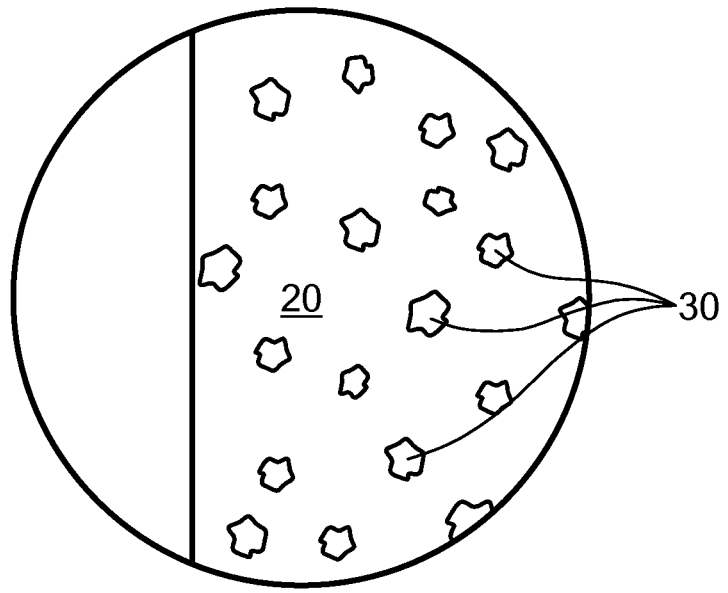
FIG. 1D is an enlargement of a portion of FIG. 1A.

This application incorporates by reference the entire disclosure of U.S. Provisional Application No. 62/028,880, filed on Jul. 25, 2014, entitled "Biomaterial for Response Assessment and Nodal Detection (BRAND)".

The present approach relates to labeling metastatic or circulating tumor cells (biomarkers) at a source or primary tumor, for enhanced detection and isolation efficiency and for treatment. In this approach, one or more biocompatible implants are loaded with gold or other nanoparticles functionalized to bind tumor cell and/or with a therapeutic agent. The nanoparticles are conjugated to a tumor-targeting moiety and in some embodiments to a detection moiety, and are embedded in a biocompatible and biodegradable matrix material. The implants are placed in a region of tumor cells in a patient, for example, during radiation therapy procedures, such as external beam radiation therapy (EBRT) or brachytherapy. Once in place, the implant gradually releases the functionalized nanoparticles into the tumor as the matrix material degrades, to label circulating tumor cells (CTCs) at their source before they are shed into the blood or lymphatic vessels. The nanoparticles themselves or a detection moiety conjugated to the nanoparticles enable tracking and detection of the nanoparticles bound to the tumor cells in regions of the body to which the tumor cells have migrated. The implants can also be loaded additionally or alternatively with a therapeutic agent, such as an anti-cancer drug, to provide an additional mechanism for treating cancer or to combine radiation therapy with chemotherapy in a synchronous manner.

In some embodiments, the implants are formed in shapes that correspond to the shapes of brachytherapy spacers and fiducial markers used in radiotherapy techniques. In some embodiments, the implant can be formed as a coating over a brachytherapy spacer or fiducial marker. Implantation of the implants can be accomplished using techniques from radiotherapy (RT), in which inert biomaterials (brachytherapy spacers or fiducial markers) are implanted in or next to tumor cells to ensure spatial accuracy of implanted radioactive seeds or guidance of an external radiation source. The implantation of the present implants can occur simultaneously with implantation of the brachytherapy spacers or fiducial markers during RT practice, which adds no or minimal additional inconvenience to patients. The implants shaped as or coated on brachytherapy spacers or fiducial markers can be used to load an anti-cancer therapeutic agent to provide an additional mechanism for treating cancer.

The present approach provides the ability to track CTCs from a source or primary tumor via either blood vessel or lymph system routes to distant metastatic sites. The approach can enhance detection efficiency. The approach can also enhance understanding of cancer progression or metastasis. Implantation incurs no additional inconvenience to a patient already undergoing radiotherapy or brachytherapy. This approach provides a departure from current approaches that try to find and label CTCs after they are already in circulation.

One embodiment of an implant 10 is illustrated schematically in FIGS. 1A-1D. The implant includes a matrix material 20 comprising a biocompatible and biodegradable polymer. A plurality of nanoparticles 30 functionalized to bind tumor cells are dispersed within the matrix material. (FIGS. 1A, 1D) As the polymer degrades over time, the nanoparticles are released (FIGS. 1B, 1C), enabling them to bind to neighboring tumor cells.

Figure 2:
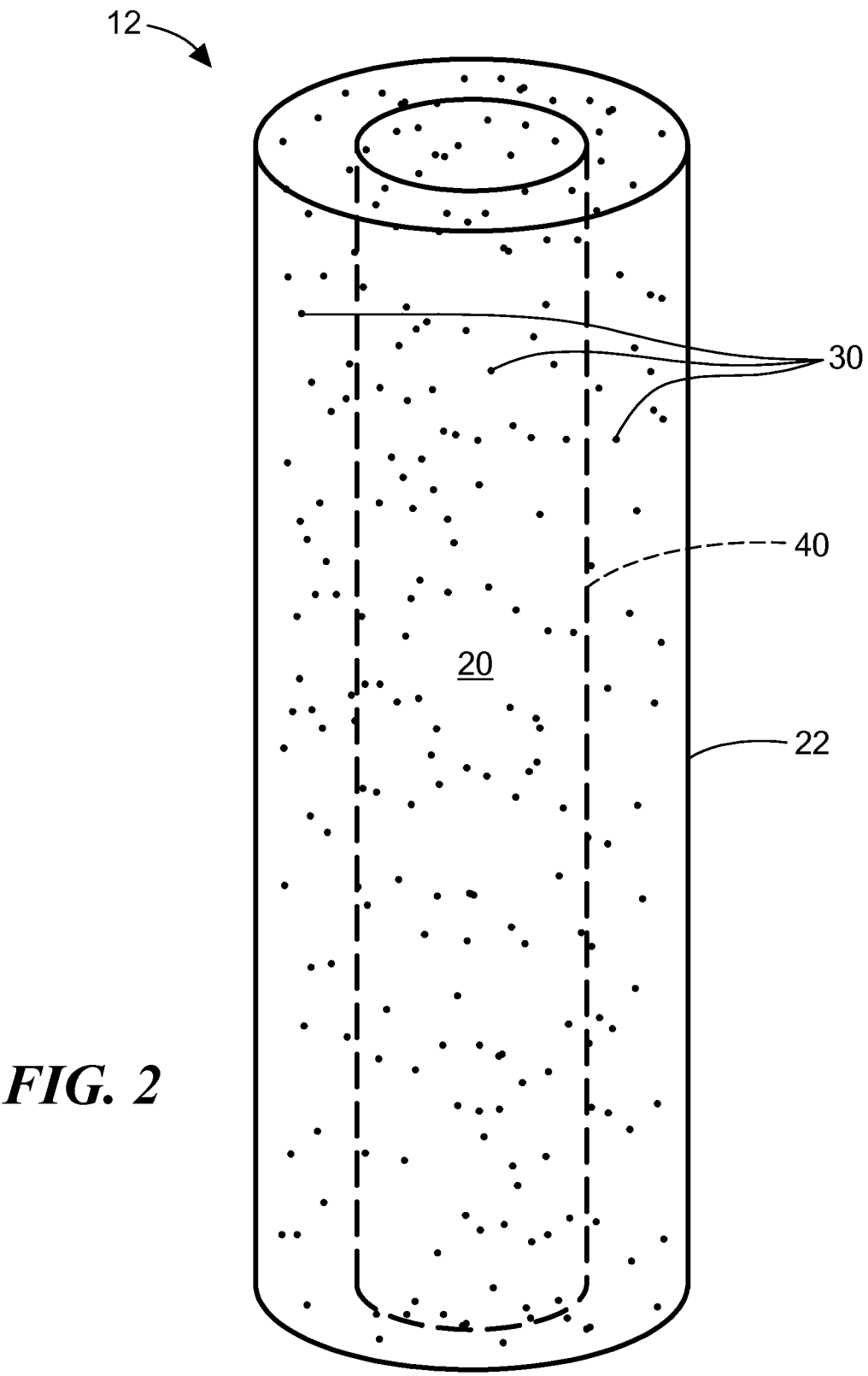
FIG. 2 is a schematic illustration of a further embodiment of an implant with a brachytherapy spacer core.

Another embodiment of an implant 12 is illustrated schematically in FIG. 2. The matrix material 20 with embedded functionalized nanoparticles is formed as a coating 22 over a brachytherapy spacer 40 or radiotherapy fiducial marker. The brachytherapy spacers are typically formed of a biologically inert material such as an acrylic resin, polyacrylate, or polyethylene. The fiducial markers are typically formed of a radio opaque material. As the polymer coating degrades, the nanoparticles are released, enabling them to bind to neighboring tumor cells.

Figure 3A:
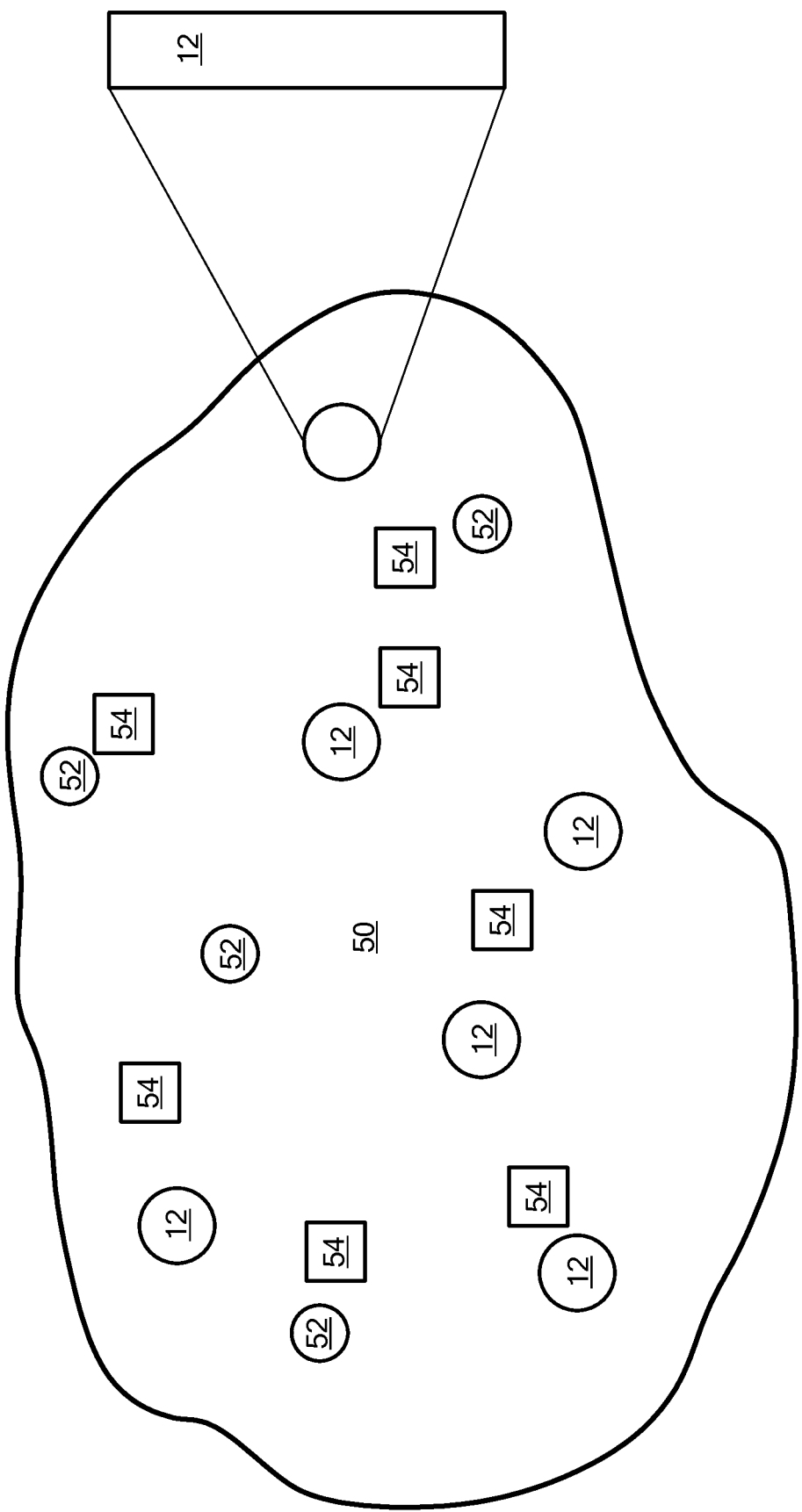
FIG. 3A is a schematic illustration of implants implanted in a region of tumor cells.
Figure 3B:
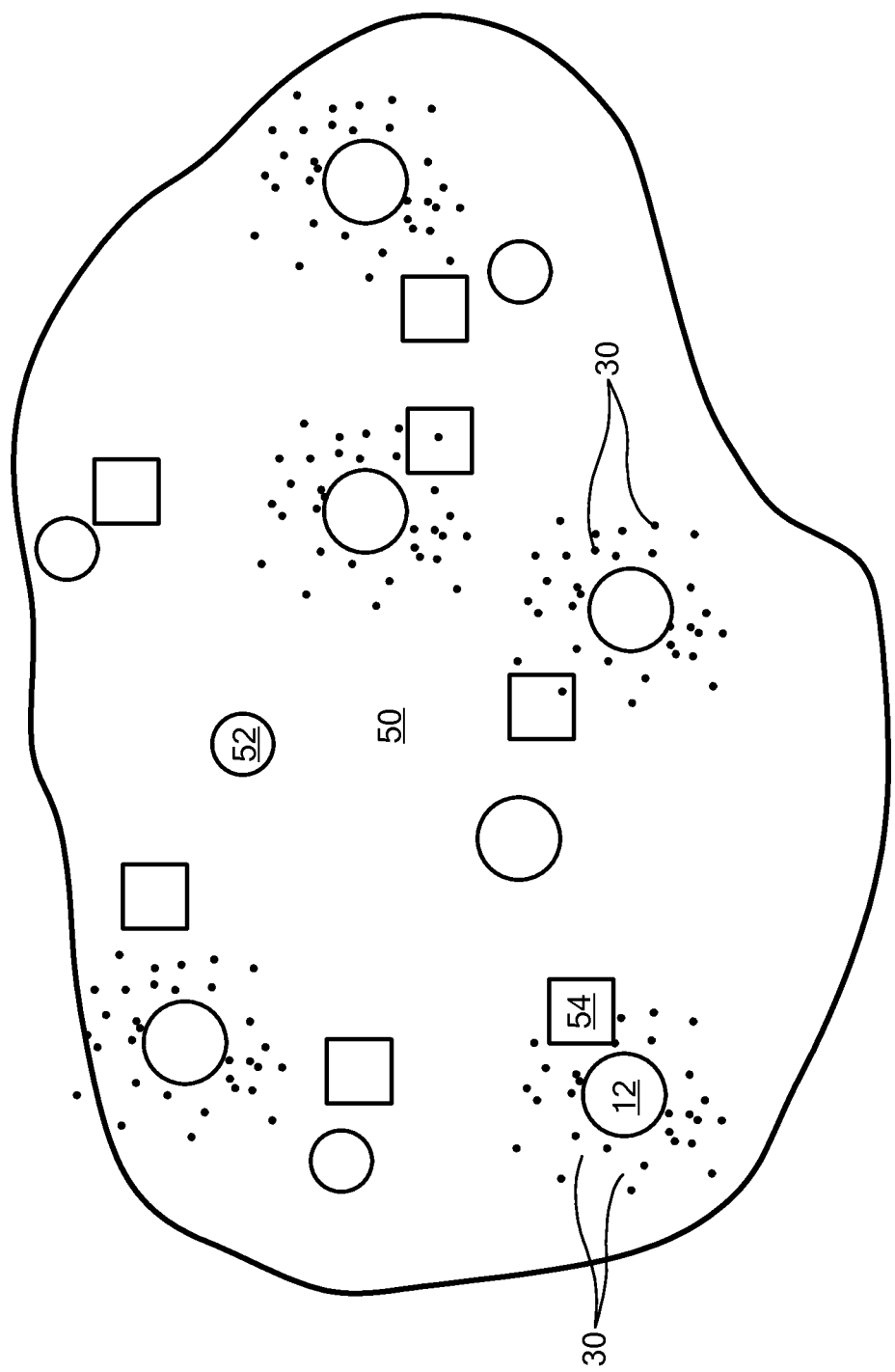
FIG. 3B is a schematic illustration of the implants of FIG. 3A degrading over time to release functionalized nanoparticles.

FIG. 3A illustrates an embodiment in which implants in the form of coated brachytherapy spacers are inserted into a region 50 of tumor cells. In a conventional brachytherapy procedure, brachytherapy spacers 52 are inserted into the tumor cells along with radioactive seeds 54 to ensure spatial accuracy of the radioactive seeds. The spacers and seeds are typically loaded into a syringe, which is used by a surgeon to inject the spacers and seeds in a desired order and a desired placement into the region of tumor cells, as specified by a treatment plan. The implants 12 can be loaded into the syringe and inserted in addition to or in place of the conventional brachytherapy spacers. FIG. 3A illustrates a region 50 of tumor cells in which implants 12 and brachytherapy spacers 52 have been inserted along with radioactive seeds 54. Over a period of time, the matrix material degrades, releasing the nanoparticles into the region of tumor cells, indicated schematically in FIG. 3B.

Figure 3C:
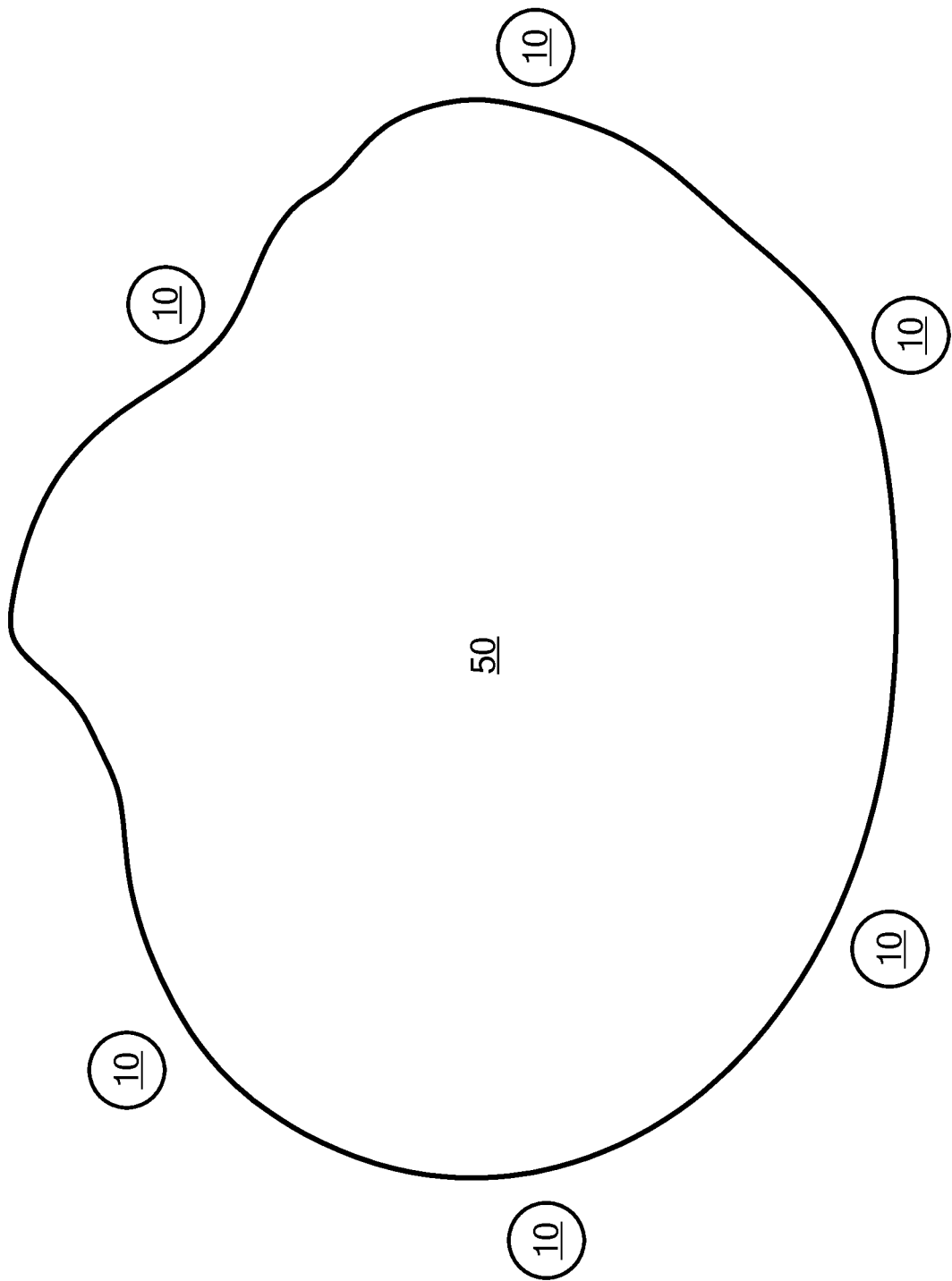
FIG. 3C is a schematic illustration of implants implanted adjacent to a region of tumor cells.

In another embodiment, the implants can be inserted adjacent to or surrounding a group of tumor cells, for example, along with or in place of fiducial markers that are used to guide external radiation therapy. FIG. 3C illustrates a region 50 of tumor cells adjacent to which a plurality of implants 10 has been placed. A region of tumor cells thus includes the space within a group of tumor cells and the space adjacent to a group of tumor cells.

The implant can have any suitable size and shape. In some embodiments, the implant can have a shape of a rod, a cylinder, a bar, a cube, a rectangle, a sphere, a shell or an ellipse. Rod-, cylinder-, or bar-shaped implants can have dimensions similar to the dimensions of a brachytherapy spacer or fiducial marker. In some embodiments, the implant be elongated and can have a length ranging from about 2 mm to about 8 mm and a diameter or shortest width ranging from about 0.5 mm to about 1.5 mm. In some embodiments, the length can be about 5 mm. In some embodiments, the diameter can be about 0.8 mm. In some embodiments, the implant is elongated and has an aspect ratio of shortest dimension to longest dimension ranging from 0.05 to 0.75. In some embodiments, the diameter can be sized to fit within a brachytherapy needle, such as an 18 G needle. In embodiments in which the matrix material is coated on a brachytherapy spacer or fiducial marker, the coating can have a thickness ranging from 0.1 mm to 1 mm. In some embodiments, the coating can have a thickness lesser than 0.1 mm or a thickness greater than 1 mm. In some embodiments, the implant can be in the form of a shell or a coating over a spherical core of inert material.

In other embodiments, the implant can be in the form of a gel in which the nanoparticles are dispersed. The gel can be injected into the region of tumor cells. Gels can include, without limitation, polyethylene glycol (PEG), polyacrylic acid (PAA), polyacrylamide, poly(N-isopropylacrylamide), hyaluronic acid, and combinations thereof.

Any suitable biocompatible and biodegradable polymer can be used as the matrix material. In some embodiments, the matrix material can be a polymer or co-polymer of lactide, glycolide, or a combination thereof. In other embodiments, the matrix material can be a polyester of hydroxycarboxylic acids. In some embodiments, the matrix material can be a polylactide, polyglycolide, polylactide co-glycolide (PLGA), polyester amide of glycolic or lactic acids, poly(N-isopropylacrylamide), polygalactin, polydioxanone, polyester, polyacrylate, polymethacrylate, polyvinyl alcohol, polyether, polyamine, chitosan, or a combination thereof.

Any suitable nanoparticle can be used that can be functionalized to bind tumor cells. In some embodiments, the nanoparticles can be gold, gadolinium, or iron oxide. The nanoparticles can have any shape, such as a sphere, rod, cube, ellipse, core-shell, and the like. The functionalized nanoparticles typically have a diameter that ranges from about 1 nanometer to about 999 nanometers. In some embodiment, the concentration of the nanoparticles in the matrix material can range from 0.001 to 10 mg per implant. In some embodiments. the concentration of the nanoparticles per implant can range from 0.001 to 0.01 mg; from 0.01 to 0.1 mg; from 0.1 to 1.0 mg; or from 1.0 to 10 mg.

The nanoparticles are conjugated to a tumor-targeting moiety. The tumor-targeting moiety can be a tumor-targeting ligand, peptide, protein, aptamer, oligonucleotide, antibody, cell adhesion molecule, or small molecule. A "small molecule" as used herein refers to an organic molecule, such as a drug or metabolite, which is less than 1000 molecular weight, and which binds to a target, such as a protein or nucleic acid, within or on the surface of a tumor cell. A tumor-targeting ligand can be folic acid, a single-chain variable fragment antibody, a ligand for epidermal growth factor receptor, transferrin, an arginylglycylaspartic acid (RGD) peptide, riboflavin, a prostate specific membrane antigen (PSMA) aptamer, or a galactose derivative. As the nanoparticles are released from the degrading matrix material, they can bind to tumor cells. If the tumor cells subsequently enter a blood vessel or lymph vessel, node, or organ, or migrate to a metastatic site, they can be detected by detecting the nanoparticles bound to them.

The release of the nanoparticles from the matrix material can be customized by modifying the polymer degradation rate to release the nanoparticles over a period of time. For example, the degradation rate can be controlled by varying one or more of, for example, the degree of cross-linking in the polymer matrix material, the molecular weight of the polymer matrix material, or the size and concentration of the nanoparticles. In other examples, the release rate can be controlled by the inclusion of an inert material such as silica or a bone material such as hydroxyapatite, a calcium salt, or a phosphate salt. In some embodiments, for example, the release rate can be selected to continue beyond the duration of a course of radiotherapy treatments. In some embodiments, the release rate can be from 1 to 5 days, 1 to 10 days, 1 to 20 days, 1 to 60 days, or 1 to 120 days.

Detection of the nanoparticles that have bound to tumor cells and migrated to other regions of a patient can be performed using any suitable imaging modality. In some embodiments, detection can be performed by use of photoacoustic imaging, surface enhanced Raman spectroscopy, X-ray computed tomography, magnetic resonance imaging, positron emission tomography, single-photon emission computed tomography, fluorescence imaging, optical coherence tomography, or ultrasound imaging. Imaging can be achieved synchronously or asynchronously. The nanoparticles can be detected in tumor cells in a blood vessel, in a lymphatic vessel, in a lymphatic node, in a lymphatic organ, or at a metastatic site in a region of the patient to which the tumor cells have migrated. Detection can occur in any desired period of time after implantation of the implants, such as about 1 day, 1 week, 1 month, 3 months, 6 months, or any period of time within or beyond these times.

In some embodiments, the nanoparticles themselves can be detected by an imaging modality. In other embodiments, the nanoparticles can be conjugated with a detection moiety that can be detected by an imaging modality. For example, the nanoparticles can be conjugated to a fluorophore, a radiolabel, or a contrast agent. In some embodiments, the tumor-targeting moiety and the detection moiety can be embodied in a single molecule.

In one embodiment, the nanoparticles can be conjugated with a fluorophore or fluorescent dye for detection using fluorescence imaging. Fluorescent dyes can include, for example and without limitation, Alexafluor derivatives (such as AF47) or derivatives of cyanine dye (such as Cy7.5).

In another embodiment, the nanoparticles can be conjugated with rhodamine B or 4-mercaptobenzoic acid, for detection using surface enhanced Raman spectroscopy.

In another embodiment, the nanoparticles can be conjugated with poly(lactic acid), for detection using ultrasound imaging.

In another embodiment, the nanoparticles can be gold nanoparticles, for detection using X-ray computed tomography.

In another embodiment, the nanoparticles can be gadolinium or iron-oxide nanoparticles, for detection using magnetic resonance imaging.

Figure 1E:
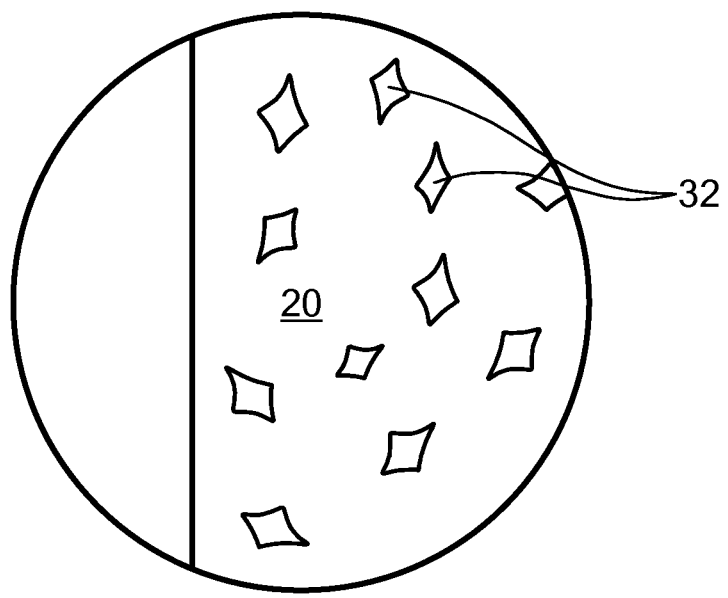
FIG. 1E is a partial view of an implant with a polymer matrix and a therapeutic agent.

In another aspect, the implant can also include a therapeutic agent dispersed within the matrix material in addition to the functionalized nanoparticles. FIG. 1E schematically illustrates a portion of an implant in which a therapeutic agent 32 is dispersed with a matrix material 20. The therapeutic agent can be an anti-cancer drug, such as without limitation, docetaxel, paclitaxel, doxorubicin, cisplatin, or gemcitabine, most hydrophobic drugs, anti-androgen compounds, small molecule signaling pathway inhibitors, or a combination thereof. Anti-androgen compounds can include, for example, enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, or cimetidine. Small molecule signaling pathway inhibitors can include, for example, PI3K inhibitors, PARP inhibitors, or PI3K/AKT/mTOR pathway inhibitors. The therapeutic agent can be present in the matrix material at a concentration ranging from 250 to 500 µg/mm length of implant for an implant diameter ranging from 0.5 mm to 1.5 mm. In some embodiments the concentration can be lower than 250 µg/mm length of implant, and in some embodiments, the concentration can be greater than 500 µg/mm length of implant. The therapeutic agent can also be released from nanoparticles, providing a dual release mechanism.

In a further aspect, the implants in the form of brachytherapy spacers or radiotherapy fiducial markers can include a therapeutic agent dispersed within the matrix material. The therapeutic agent can be an anti-cancer drug, such as without limitation, docetaxel, paclitaxel, doxorubicin, cisplatin, gemcitabine, most hydrophobic drugs, anti-androgen compounds, small molecule signaling pathway inhibitors, or a combination thereof. Anti-androgen compounds can include, for example, enzalutamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, or cimetidine. Small molecule signaling pathway inhibitors can include, for example, PI3K inhibitors, PARP inhibitors, or PI3K/AKT/mTOR pathway inhibitors. The therapeutic agent can be present in the matrix material at a concentration ranging from 250 to 500 µg/mm length of implant for implants with diameters ranging from 0.5 mm to 1.5 mm. In some embodiments the concentration can be lower than 250 µg/mm length of implant, and in some embodiments, the concentration can be greater than 500 µg/mm length of implant.

The implants can be fabricated in any suitable manner. In one embodiment, the implants can be fabricated by providing a mixture of a matrix material and nanoparticles functionalized to bind tumor cells in an appropriate solvent system. Additionally or alternatively, the mixture can also include a therapeutic agent, such as an anti-cancer drug. Any other components, such as a binder, can be included. In one embodiment, a binder can be polyacrylamide. The implant can include an inert material selected to tune release properties, such as silica or a bone material. The bone material can include, for example, hydroxyapatite, a calcium salt or a phosphate salt.

In one embodiment, the mixture is provided as a viscous slurry that can be formed into a body of an appropriate shape for the implant, such as an elongated shape. In one embodiment, the mixture is formed into a tube, for example, by infusing the mixture into a length of silicon tubing using an infusion pump or by extrusion of the mixture. The tube or extrusion is solidified, such as by drying. The solidified tube or extrusion is cut into segments of an appropriate length or lengths. In another embodiment, the mixture is placed into appropriate molds having a desired shape for the implants.

Implants can be fabricated with nanoparticle formulations that can be used in personalized treatment plans. Nanoparticles can be pre-functionalized with a detection moiety, such as an imaging agent, and a tumor-targeting moiety, such as an antibody or peptide, specific for a patient tumor type. One example includes the synthesis of gold nanoparticles (GNPs) with heterobifunctional polyethylene glycol (PEG) (in varying ratios) to impart different functional groups that can be used later to conjugate a variety of tumor-targeting and detection moieties.

Figure 6:
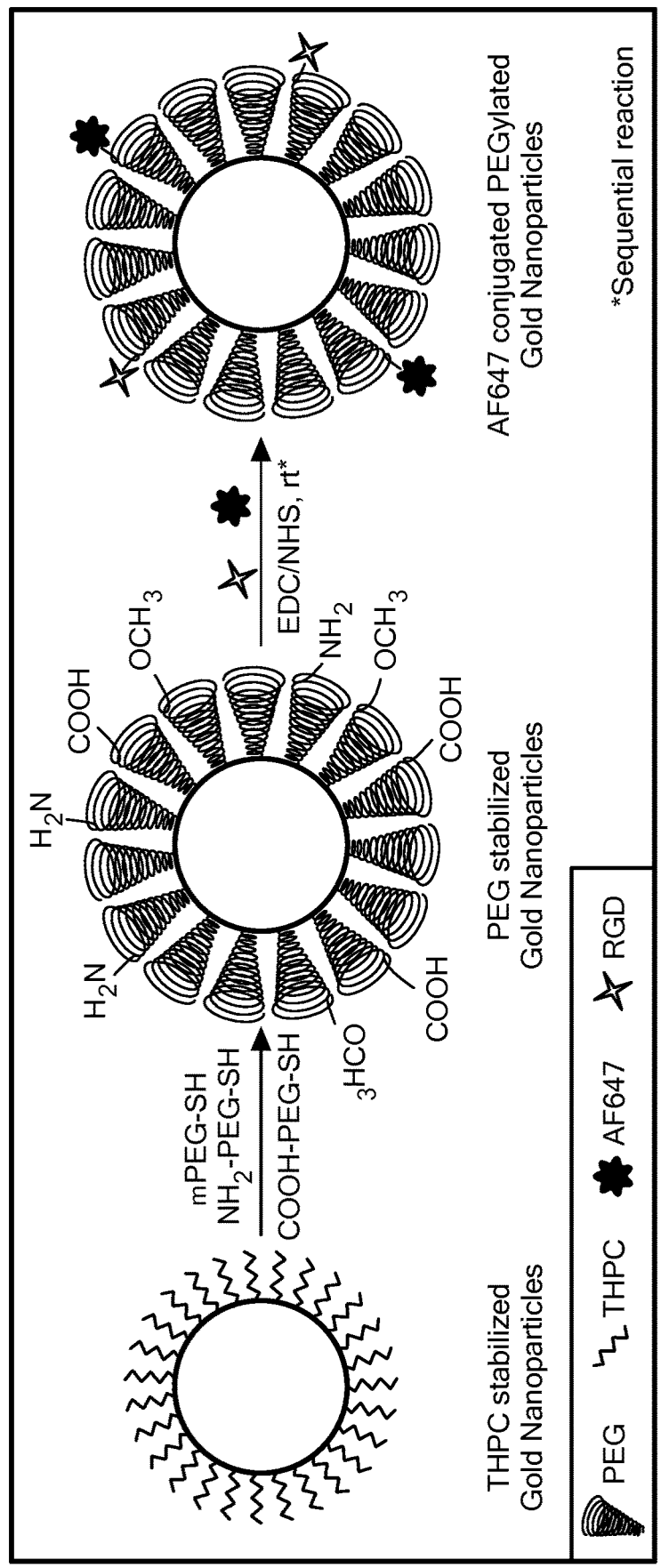
FIG. 6 is a schematic image of a pre-functionalization of gold nanoparticles.

Referring to FIG. 6, gold nanoparticles can be pre-functionalized with heterobifunctional PEGs using a simple ligand exchange process. (Kumar et al. Translational Cancer Research. 2013, 2(4), 228-239) Three heterobifunctional PEGs, namely, methoxy-PEG-thiol (Mw: 2,000 Da), amine-PEG-thiol (Mw: 3,400 Da), and carboxymethyl-PEG-thiol (Mw: 2,000 Da) can be incubated with GNPs to obtain nanoparticles pre-functionalized with —$OCH_3$ (methoxy), —$NH_2$ (amine), and —COOH (carboxyl) groups.

The free amine group on the GNP surface can be used to covalently conjugate an imaging agent using a succinimidyl ester of fluorophore or radiolabel in a basic medium.

The carboxyl groups on the GNP surface can be conjugated with a targeting agent such as an antibody or peptide specific for a particular tumor type using carbodiimide chemistry. The carboxyl groups can be activated using known water soluble cross linker 1-Ethyl-3-(3-dimethylaminopropyl)carbodiimide, which readily reacts with primary amines (from antibodies or peptides) to form stable amide bonds.

The implants can also be customized to different patients or treatment schedules by varying the degradation rate of the polymer matrix material, and the nanoparticle size, shape, or functionalization. Nanoparticles can themselves contain nanoparticles to provide a dual release profile.

The implants can be used in clinical applications in which inert spacers are currently employed in the clinic. The present implants are advantageous in that they can expand the range of clinical applications to include the early detection of disease aggressiveness or metastasis, prognosis or treatment response assessment.

The implants can also be provided in kit form with a needle for injecting the implant into a region of tumor cells. The needle can be a brachytherapy needle. The kit can also include radioactive brachytherapy seeds and optionally brachytherapy spacers.

The implants can be placed in a variety of types of tumor cells, including tumor cells from prostate cancer, lung cancer, pancreatic cancer, liver cancer, breast cancer, ovarian cancer, gastric cancer, colon cancer, brain cancer, and head and neck cancer.

The implants and methods described herein can provide one or more advantages in various applications. Release of the functionalized nanoparticles can enable labeling of tumor cells directly at the source or primary tumor, which can yield a high number of labeled cells, including tumor stem cells which do not express a given marker. The functionalized nanoparticles enable detection of migrating tumor cells via one or more different imaging modalities. Functionalized nanoparticle labeling of cells can be used to investigate cell migration. The functionalized nanoparticles are relatively non-toxic and biocompatible. The implants can also be used to load other therapeutic agents, such as anti-cancer drugs.

The approach can take advantage of a morphological similarity to the clinically-used brachytherapy spacers and fiducial markers. No additional surgical intervention is required to implant the implant at diseased sites.

A variety of nanomaterials can be employed to provide image contrast and help with enhanced detection and isolation of CTCs. The approach can be applied during radiotherapy treatment that currently employs inert biomaterials. The approach can employ biodegradability of the biomaterials as opposed to non-degradable implants like metallic gold fiducials.

The implants can be applied to any disease site, such as the lung, prostate, liver, pancreas, and the like, that can employ radiotherapy implants during treatment to serve the additional function of labeling tumor cells. Gold and other high atomic number nanoparticles can be used to enhance brachytherapy through interaction with photons from the radioactive seeds to induce photoelectrons/Auger electrons.

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

Example 1

In one example, 250-300 mg of PLGA was dissolved in a minimum amount of dimethyl sulfoxide (DMSO). Docetaxel was dissolved in DMSO, and the two solutions were mixed using sonication to obtain a viscous uniform slurry. The slurry was transferred to a 1 ml syringe using a Luer stub adapter (0.5 in; 18 G) attached to a silicon tube (inner diameter 0.8 mm). The paste was infused at a predetermined flow rate into the silicon tubing using an infusion pump. The tube was dried overnight at 45-50° C. The crystallized implants were taken out of the tubing using brachytherapy stubs, cut into 5 mm lengths, and stored at room temperature in the dark.

Example 2

Figure 4A:
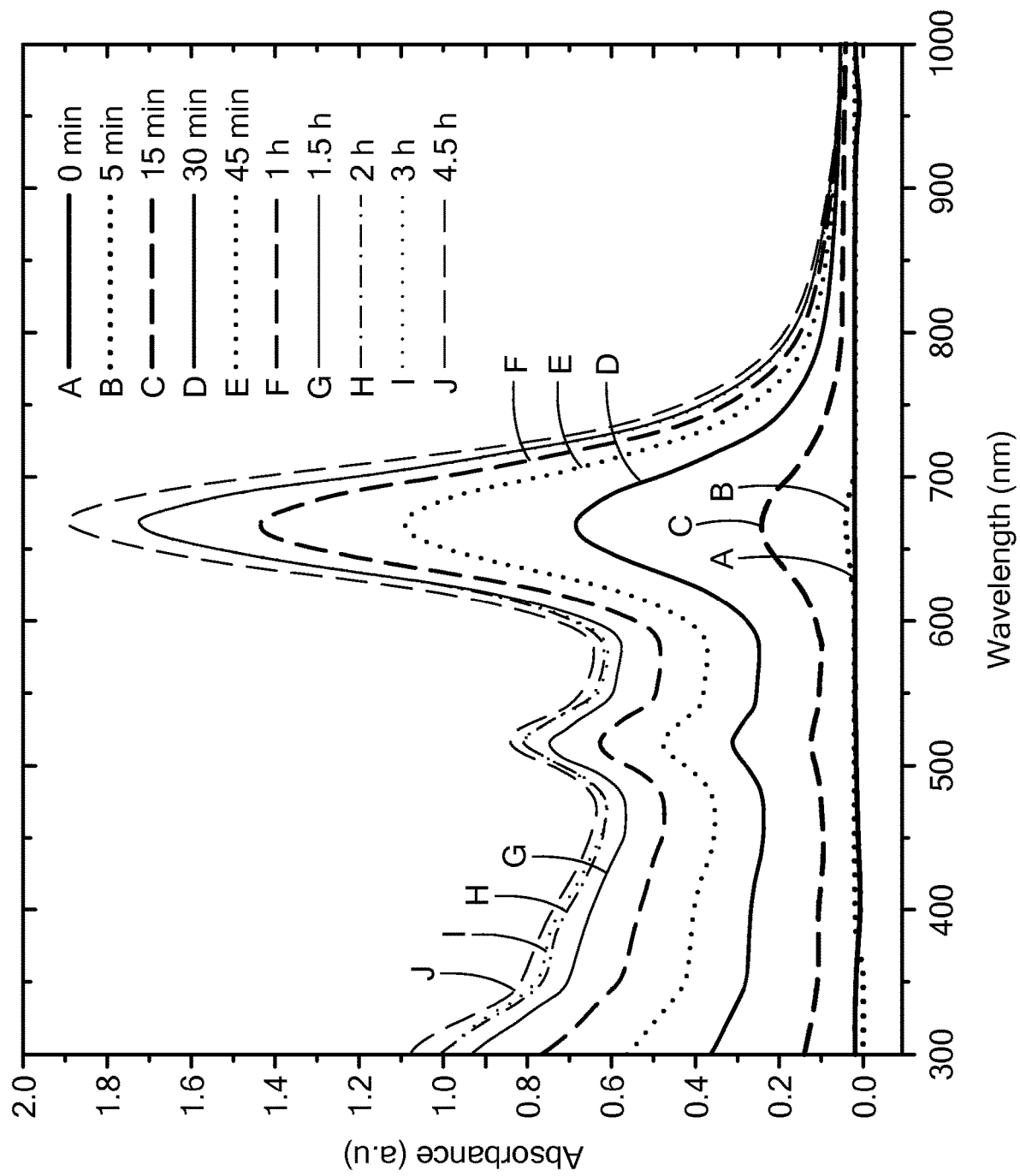
FIG. 4A is a graph of an in vitro release of gold nanoparticles from an implant monitored by UV-Vis spectroscopy over time.
Figure 4B:
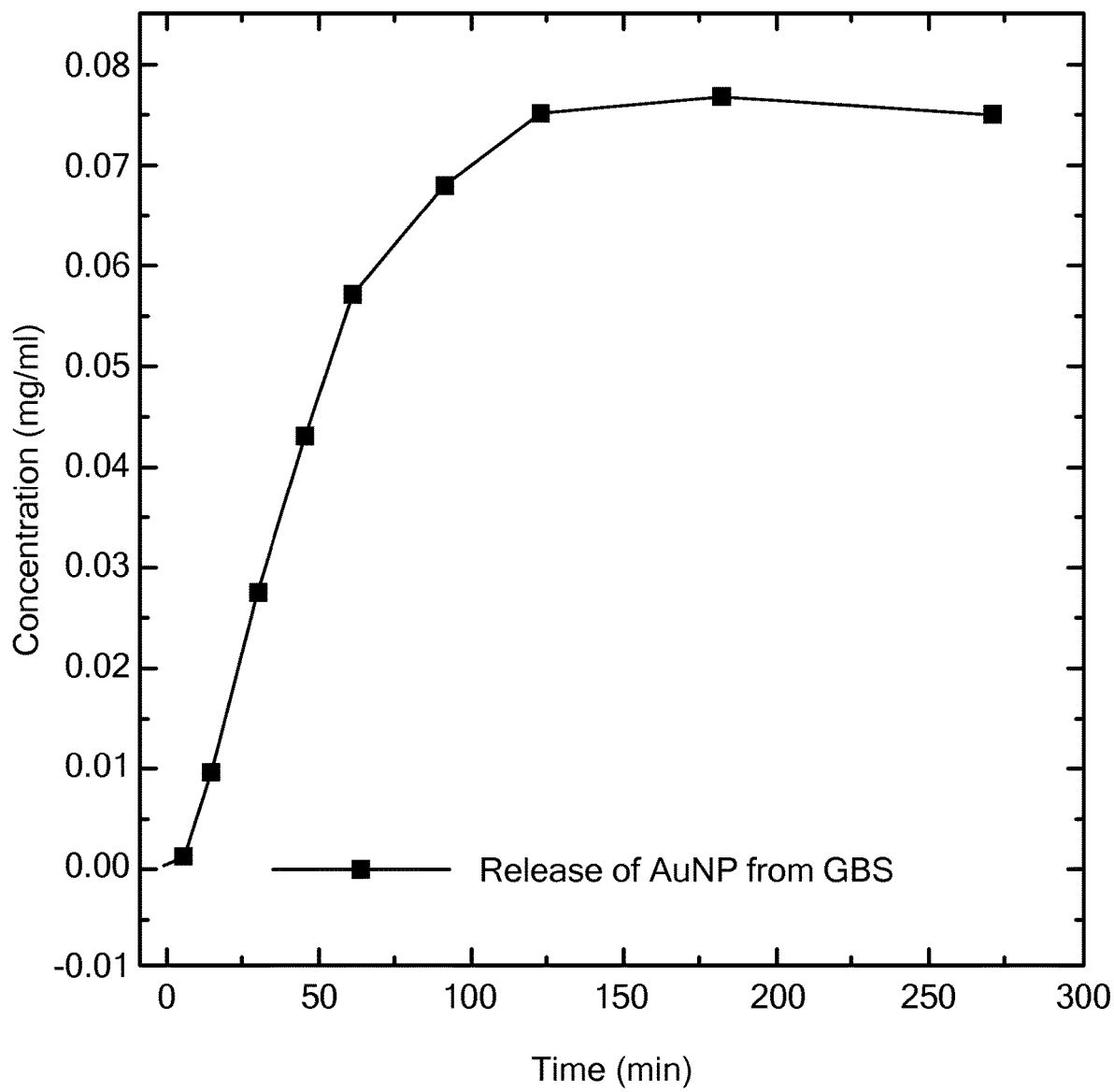
FIG. 4B is a graph of a concentration profile the gold nanoparticles released in FIG. 4A over time.
Figure 5:
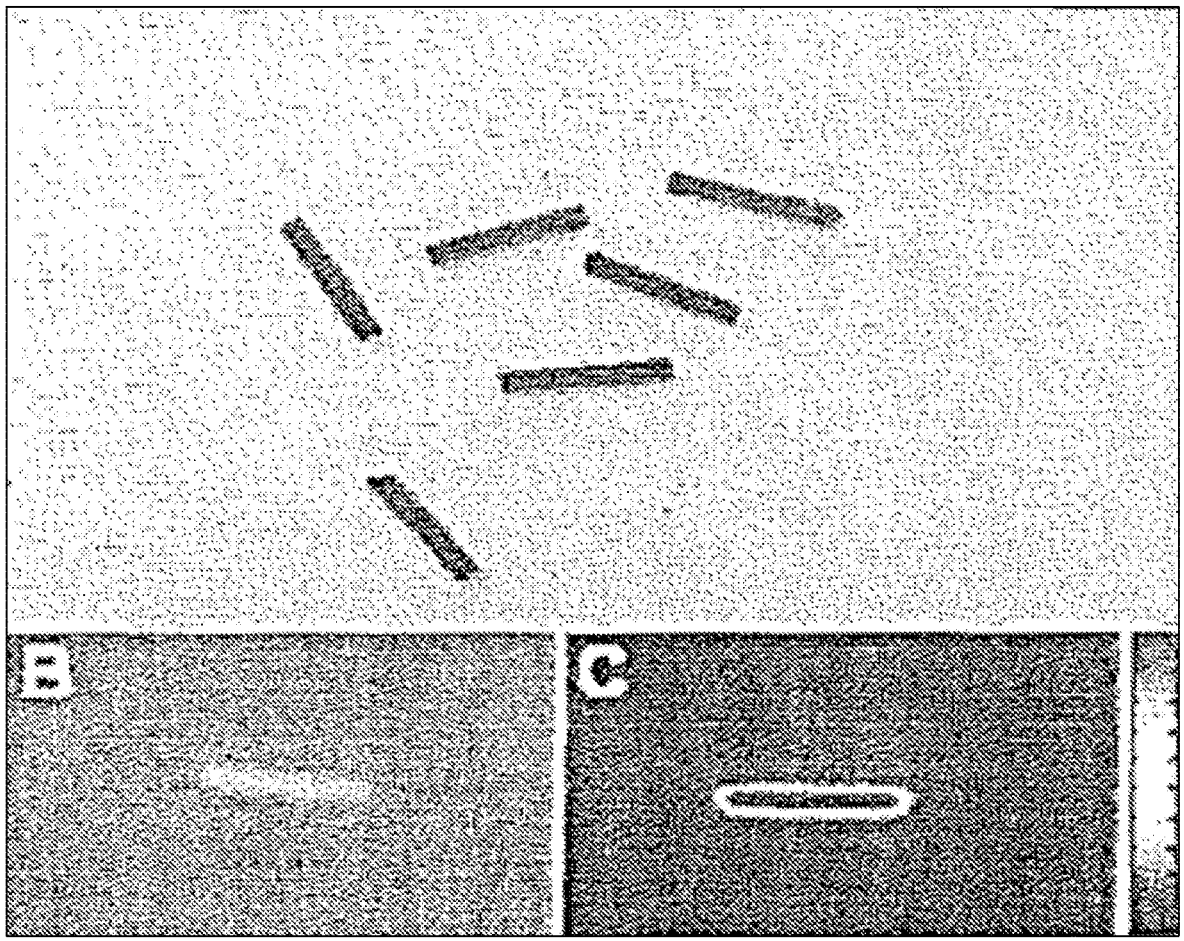
FIG. 5 shows images of fabricated implants employing fluorescent gold nanoparticles in which the top image is an image of the implants, image B is a CT image of the implants implanted in a tissue mimic (super flab), and image C is an optical fluorescence image of the implant.

A prototype implant with fluorescent gold nanoparticles embedded in PLGA was fabricated and implanted in a tissue mimic. The tissue mimic was provided by the material commercially available as SuperFlab. FIG. 4A illustrates an in vitro release of the fluorescent gold nanoparticles from the implant monitored using UV-visible spectroscopy over time, from 0 minutes to 4.5 hours. FIG. 4B shows the corresponding concentration profile over time. The prototype implants are shown in the top image of FIG. 5. Image B shows a CT image of the implant in the tissue mimic, and image C shows an optical fluorescence image of the implant in the tissue mimic.

Example 3

Implants were fabricated with the drug docetaxel (DTX) dispersed within a PLGA matrix material as described in Example 1 above. The implants (also called spacers in the study) were implanted in tumors in PC3 tumored mice. Four groups were tested: a control group that was not treated; a control group with "blank" implants (implants that contain no drugs or functionalized nanoparticles); a group that received the drug DTX intravenously only; and a group that received implants loaded with the drug DTX.

Figure 7A:
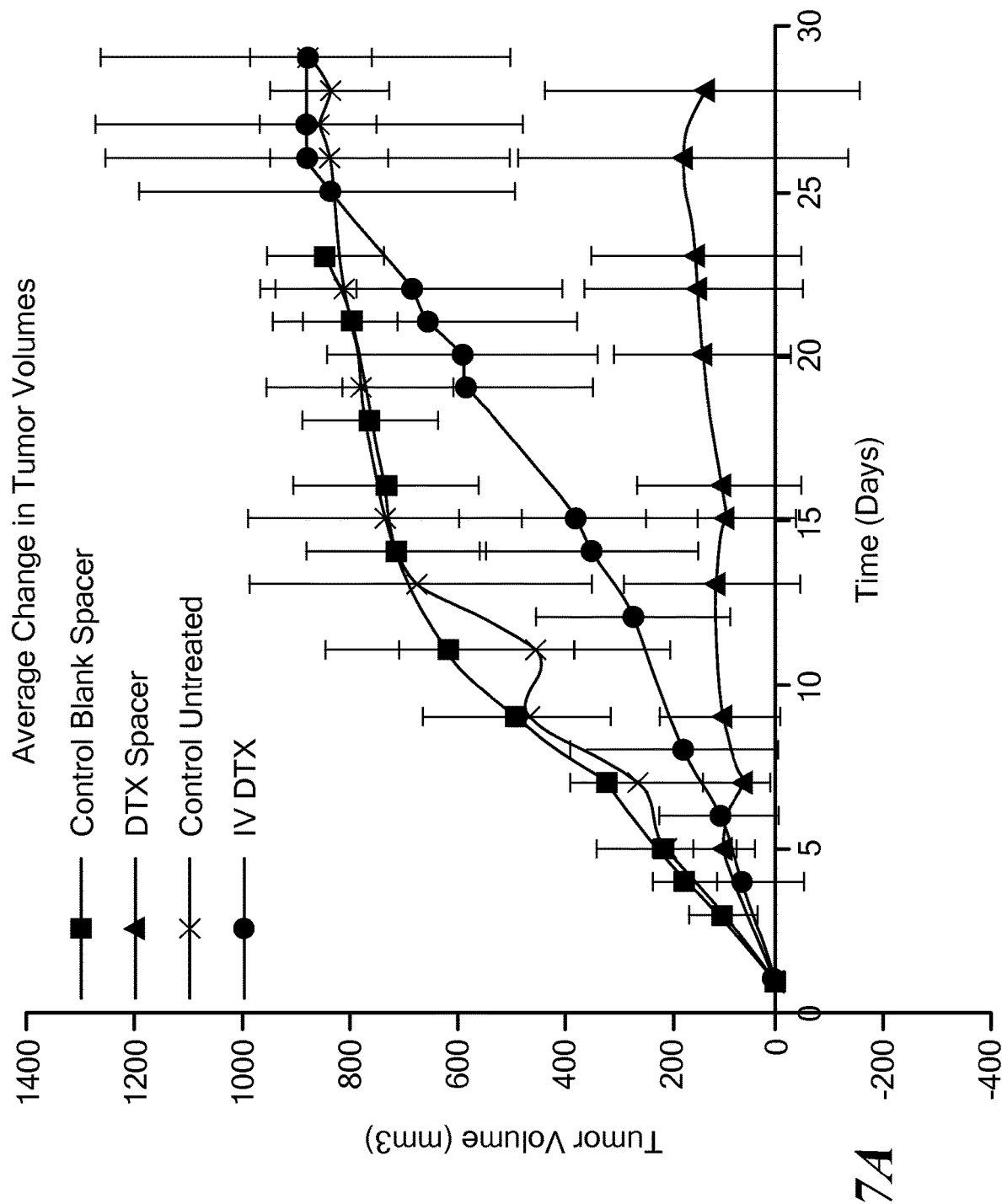
FIG. 7A is a graph of average change in tumor volumes in four mouse groups in a first study of the present implants.
Figure 7B:
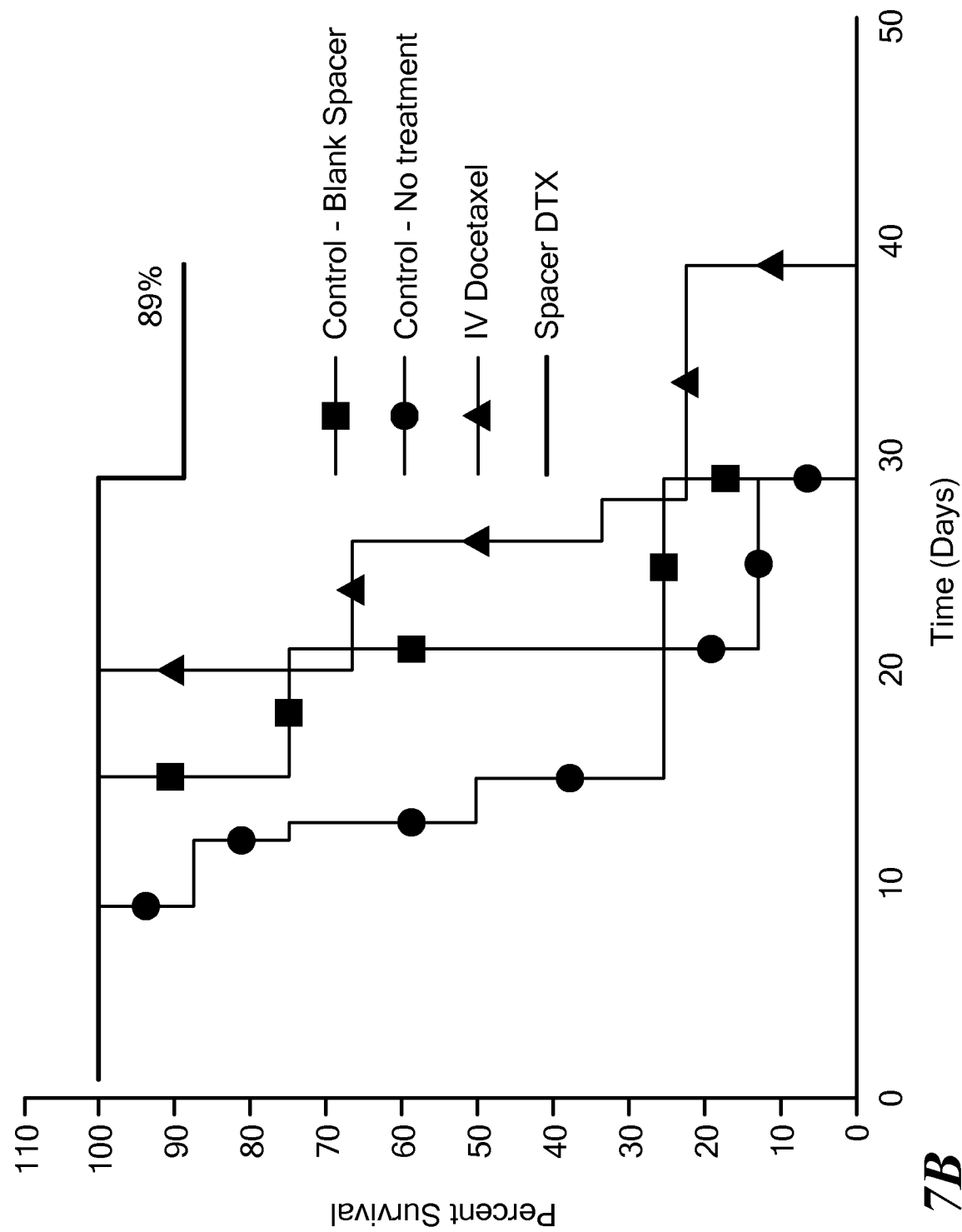
FIG. 7B is a graph of Kaplan-Meier survival curves for the four mouse groups in FIG. 7A.

The implants were found to inhibit tumor growth and shrink the tumor as the drug was released intratumorally with minimal visible adverse effects to the mice. See FIG. 7A, which illustrates the average change in tumor volumes over time. 89% of the mice with the implant loaded with DTX survived after 40 days, whereas 0% of the mice from the other treatment groups survived at 40 days. See FIG. 7B, which illustrates Kaplan-Meier survival curves for the mice at 40 days.

Figure 8:
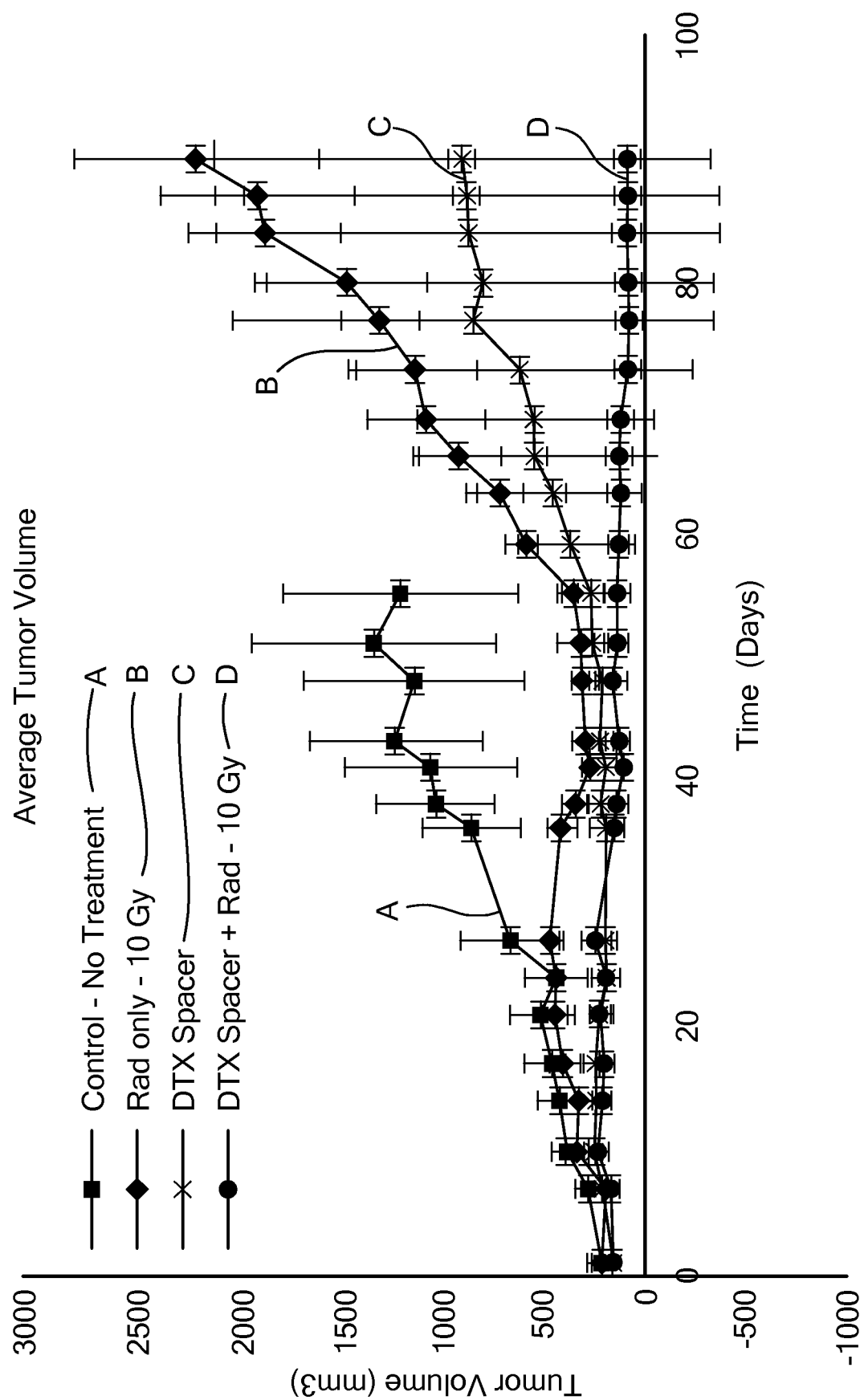
FIG. 8 is a graph of average tumor volume over time in four mouse groups in a second study of the present implants.

In a further study, mice were treated with combined chemotherapy and radiation therapy, by using implants loaded with docetaxel and external beam radiation. Four groups were tested: a control group that received no treatment; a group that received external radiation only; a group that received the docetaxel-loaded implant only; and a group that received both external radiation and the docetaxel-loaded implant. FIG. 8 illustrates average tumor volume for the different groups. Tumor volume as measured over time was least for the group that received the combined docetaxel-loaded implant and external radiation. Tumor volume as measured over time was next least for the group that received the docetaxel-loaded implant only. Tumor volumes were greater for the other two groups.

Figure 9A:
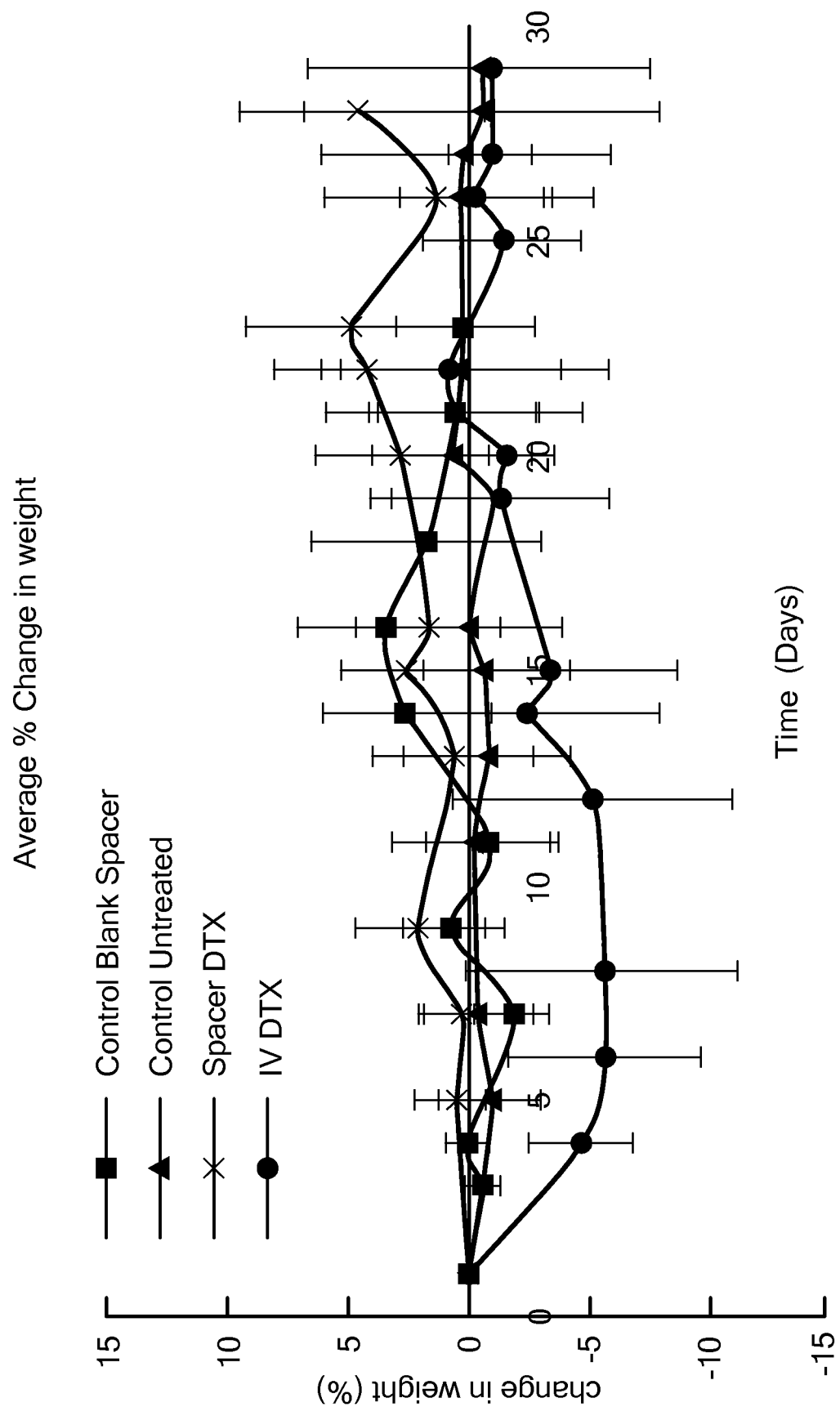
FIGS. 9A and 9B are graphs of average percent change in weight of the mouse groups in the first and second studies.
Figure 9B:
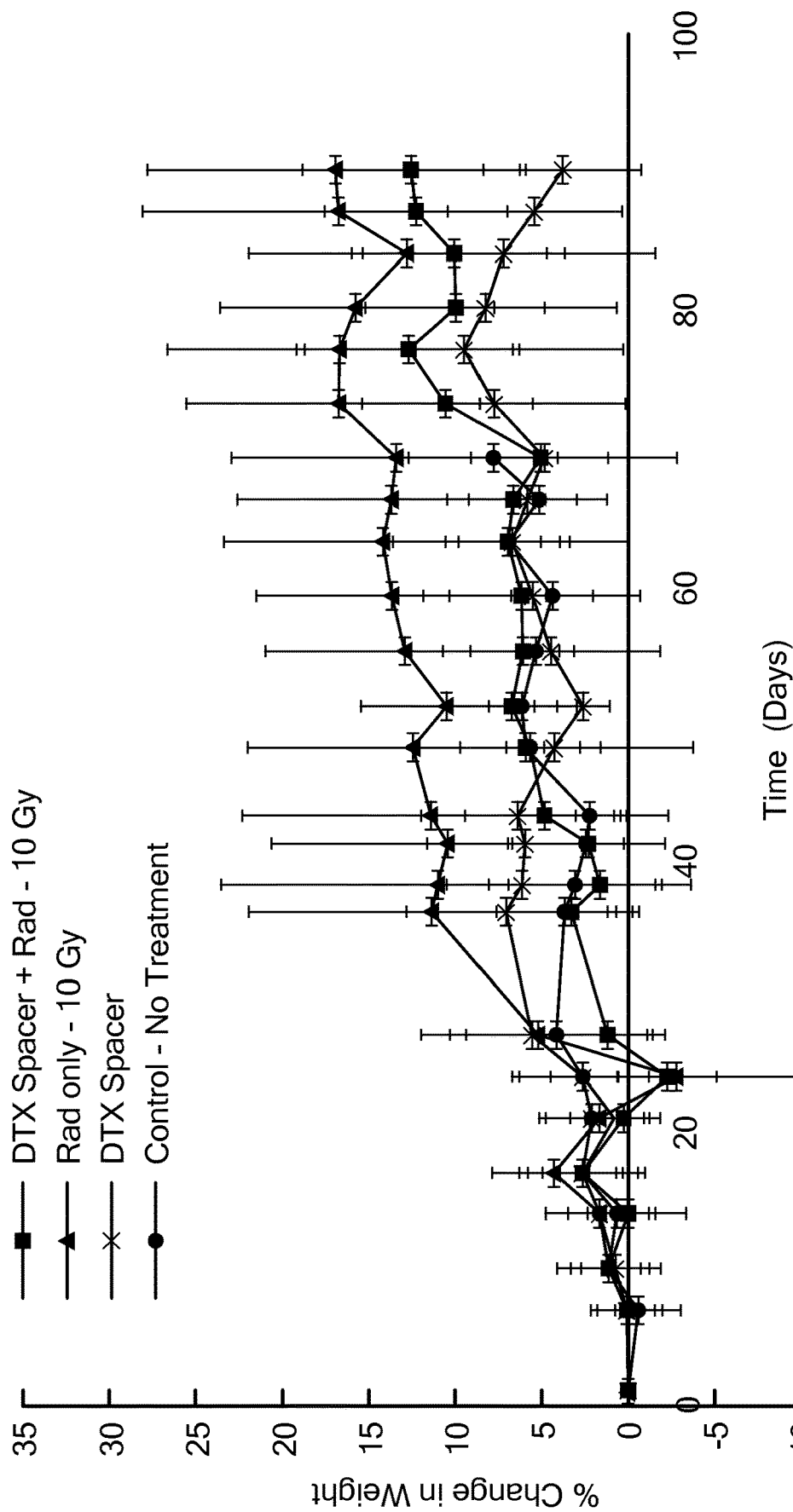

Toxicity measurement studies were carried out by measuring changes in body weight for the different groups for both studies. FIGS. 9A and 9B illustrate average change in weight for the mice in both studies. No observable toxicity was found. Also, pilot immunotoxicity testing showed no changes in blood chemistries and hematology.

What is claimed is:

1. A method of detecting migration of tumor cells out of a region of tumor cells, the method comprising:
   (a) implanting one or more implants in a region of tumor cells in a patient in need thereof, the implant comprising:
      a matrix material comprising a biocompatible and biodegradable polymer, and
      a plurality of nanoparticles functionalized to bind and track said tumor cells, the functionalized nanoparticles dispersed within the matrix material, conjugated to a tumor-targeting moiety, and conjugated to a detection moiety;
   (b) waiting until nanoparticles are released from the implant, the released nanoparticles bind to tumor cells in said region, and nanoparticle-bound tumor cells migrate out of said region; and
   (c) detecting the nanoparticle-bound tumor cells after they have migrated out of said region.

2. The method of claim 1, wherein the detection moiety is selected from the group consisting of a fluorophore, a radiolabel, and a magnetic resonance contrast agent.

3. The method of claim 1, wherein the tumor-targeting moiety is selected from the group consisting of a tumor-targeting ligand, a peptide, a protein, an aptamer, an oligonucleotide, an antibody, a cell adhesion molecule, a small molecule, and combinations thereof.

4. The method of claim 1, wherein the detecting step comprises use of photoacoustic imaging, surface enhanced Raman spectroscopy, X-ray computed tomography, magnetic resonance imaging, positron emission tomography, single-photon emission computed tomography, fluorescence imaging, optical coherence tomography, or ultrasound imaging.

5. The method of claim 1, wherein the implant is a brachytherapy spacer or a radiotherapy fiducial marker.

6. The method of claim 1, wherein the implant is in form of a gel and the biocompatible and biodegradable polymer is selected from the group consisting of a polyethylene glycol, polyacrylic acid, polyacrylamide, poly(N-isopropylacrylamide), hyaluronic acid, and combinations thereof.

7. The method of claim 1, wherein the tumor cells are initially present in a primary tumor.

8. The method of claim 1, wherein the nanoparticles are detected in tumor cells in a blood vessel, in a lymphatic vessel, in a lymphatic node, in a lymphatic organ, or at a metastatic site in a region of the patient to which the tumor cells have migrated.

9. The method of claim 1, wherein the functionalized nanoparticles comprise a material selected from the group consisting of gold, gadolinium, and iron-oxide.

10. The method of claim 1, wherein the implant further comprises a therapeutic agent.

11. The method of claim 1, further comprising detecting a metastasis and treating the metastasis.

12. The method of claim 10, wherein the therapeutic agent is an anti-cancer agent.

13. The method of claim 10, wherein the therapeutic agent is selected from the group consisting of docetaxel, paclitaxel, doxorubicin, cisplatin, gemcitabine, a hydrophobic drug, an anti-androgen compound, a small molecule signaling pathway inhibitor, and combinations thereof.

14. The method of claim 13, wherein the anti-androgen compound is selected from the group consisting of enzaluamide, flutamide, nilutamide, bicalutamide, abiraterone acetate, cyproterone acetate, megestrol acetate, chlormadinone acetate, spironolactone, canrenone, drospirenone, dienogest, norgestimate, ketoconazole, cimetidine, and combinations thereof.

15. The method of claim 13, wherein the small molecule signaling pathway inhibitor is selected from the group consisting of a PI3K inhibitor, a PARP inhibitor, a PI3K/AKT/mTOR pathway inhibitor, and combinations thereof.

16. The method of claim 10, wherein the implant has a diameter ranging from 0.5 mm to 1.5 mm, and the therapeutic agent is present in the matrix material at a concentration ranging from 250 to 500 µg/mm length of the implant.

* * * * *